(12) United States Patent
Golden et al.

(10) Patent No.: US 8,529,583 B1
(45) Date of Patent: Sep. 10, 2013

(54) SURGICAL CLIP REMOVAL APPARATUS

(75) Inventors: Steve Golden, Menlo Park, CA (US);
Liem Ho, Mountain View, CA (US);
John Nguyen, San Jose, CA (US)

(73) Assignee: Medtronic, Inc., Minneapolis, MN (US)

( * ) Notice: Subject to any disclaimer, the term of this patent is extended or adjusted under 35 U.S.C. 154(b) by 1059 days.

(21) Appl. No.: 09/540,638

(22) Filed: Mar. 31, 2000

Related U.S. Application Data

(60) Provisional application No. 60/152,401, filed on Sep. 3, 1999.

(51) Int. Cl.
*A61B 17/10* (2006.01)
*A61B 17/04* (2006.01)

(52) U.S. Cl.
USPC .......................................... 606/138; 606/147

(58) Field of Classification Search
USPC ................. 606/138, 139, 148, 225, 142, 113,
606/147, 222, 219, 226, 223; 112/224, 169,
112/285; 223/99, 103; 228/57; 254/28;
81/44; 43/53.5
See application file for complete search history.

(56) References Cited

U.S. PATENT DOCUMENTS

| | | | |
|---|---|---|---|
| 43,098 A | 6/1864 | Cooper | |
| 636,728 A * | 11/1899 | Kindel | 223/103 |
| 655,190 A | 8/1900 | Bramson | |
| 1,087,186 A | 2/1914 | Scholfield | |
| 1,167,014 A | 1/1916 | O'Brien | |
| 1,539,221 A * | 5/1925 | Tennant | 228/57 |
| 1,583,271 A | 5/1926 | Biro | |
| 1,625,602 A | 4/1927 | Gould et al. | |
| 1,867,624 A | 7/1932 | Hoffman | |
| 2,201,610 A | 5/1940 | Dawson | |
| 2,240,330 A | 4/1941 | Flagg et al. | |
| 2,256,382 A | 9/1941 | Dole et al. | |
| 2,264,679 A | 12/1941 | Ravel | |
| 2,413,142 A | 12/1946 | Jones et al. | |
| 2,430,293 A | 11/1947 | Howells | |
| 2,505,358 A | 4/1950 | Gusberg et al. | |
| 2,516,710 A | 7/1950 | Mascolo | |
| 2,715,486 A | 8/1955 | Marcoff-Moghadam et al. | |
| 2,890,519 A | 6/1959 | Storz | |
| 2,940,452 A | 6/1960 | Smialowski | |
| 3,055,689 A | 9/1962 | Jorgensen | |
| 3,057,355 A | 10/1962 | Smialowski | |
| 3,082,426 A | 3/1963 | Miles | |
| 3,143,742 A | 8/1964 | Cromie | |
| 3,150,379 A | 9/1964 | Brown | |

(Continued)

FOREIGN PATENT DOCUMENTS

DE 0219999 3/1910
DE 0377052 6/1923

(Continued)

OTHER PUBLICATIONS

Emery, Robert, W., "Techniques for Minimally Invasive Direct Coronary Artery Bypass (MIDCAB) Surgery", Hanley & Belfus, Inc., Medical Publishers, p. 87-91.

(Continued)

*Primary Examiner* — Julian Woo

(57) ABSTRACT

Apparatus and methods for removing surgical fasteners. The apparatus includes a mechanism for opening the fastener so that it may be removed from, for example, tissue, prostheses or graft material.

27 Claims, 20 Drawing Sheets

(56) References Cited

U.S. PATENT DOCUMENTS

| | | | |
|---|---|---|---|
| 3,180,337 A | 4/1965 | Smialowski | |
| 3,249,104 A | 5/1966 | Hohnstein | |
| 3,274,658 A | 9/1966 | Pile | |
| 3,452,742 A | 7/1969 | Muller | |
| 3,506,012 A | 4/1970 | Brown | |
| 3,509,882 A | 5/1970 | Blake | |
| 3,547,103 A | 12/1970 | Cook | |
| 3,570,497 A | 3/1971 | Lemole | |
| 3,608,095 A | 9/1971 | Barry | |
| 3,638,654 A | 2/1972 | Akuba | |
| 3,656,185 A | 4/1972 | Carpentier | |
| RE27,391 E | 6/1972 | Merser | |
| 3,753,438 A | 8/1973 | Wood et al. | |
| 3,776,237 A | 12/1973 | Hill et al. | |
| 3,789,895 A * | 2/1974 | Levinson | 81/44 |
| 3,802,438 A | 4/1974 | Wolvek | |
| 3,825,009 A | 7/1974 | Williams | |
| 3,837,345 A | 9/1974 | Matar | |
| 3,874,388 A | 4/1975 | King et al. | |
| 3,875,648 A | 4/1975 | Bone | |
| 3,905,403 A | 9/1975 | Smith et al. | |
| 3,908,662 A | 9/1975 | Razgulov et al. | |
| 3,910,281 A | 10/1975 | Kletschka et al. | |
| 3,958,576 A * | 5/1976 | Komiya | 606/142 |
| 3,976,079 A | 8/1976 | Samuels | |
| 3,995,619 A * | 12/1976 | Glatzer | 606/138 |
| 4,006,747 A | 2/1977 | Kronenthal et al. | |
| 4,018,228 A | 4/1977 | Goosen | |
| 4,038,725 A | 8/1977 | Keefe | |
| 4,042,979 A | 8/1977 | Angell | |
| 4,073,179 A | 2/1978 | Hickey et al. | |
| 4,103,690 A | 8/1978 | Harris | |
| 4,111,206 A | 9/1978 | Vishnevsky et al. | |
| 4,129,059 A | 12/1978 | Van Eck | |
| 4,140,125 A | 2/1979 | Smith | |
| 4,170,990 A | 10/1979 | Baumgart et al. | |
| 4,185,636 A | 1/1980 | Gabbay et al. | |
| 4,192,315 A | 3/1980 | Hilzinger et al. | |
| 4,214,587 A | 7/1980 | Sakura | |
| 4,217,902 A | 8/1980 | March | |
| 4,243,048 A | 1/1981 | Griffin | |
| 4,324,248 A | 4/1982 | Perlin | |
| 4,345,601 A * | 8/1982 | Fukuda | 606/222 |
| 4,352,358 A | 10/1982 | Angelchik | |
| 4,366,819 A | 1/1983 | Kaster | |
| 4,396,139 A | 8/1983 | Hall et al. | |
| 4,416,266 A | 11/1983 | Baucom | |
| 4,456,017 A | 6/1984 | Miles | |
| 4,465,071 A | 8/1984 | Samuels et al. | |
| 4,470,415 A | 9/1984 | Wozniak | |
| 4,470,533 A | 9/1984 | Schuler | |
| 4,474,181 A | 10/1984 | Schenck | |
| 4,485,816 A | 12/1984 | Krumme | |
| 4,492,229 A | 1/1985 | Grunwald | |
| 4,522,207 A | 6/1985 | Klieman et al. | |
| 4,523,592 A | 6/1985 | Daniel | |
| 4,532,927 A | 8/1985 | Miksza | |
| 4,535,764 A | 8/1985 | Ebert | |
| 4,549,545 A | 10/1985 | Levy | |
| 4,553,542 A | 11/1985 | Schenck et al. | |
| 4,576,605 A | 3/1986 | Kaidash et al. | |
| 4,586,502 A | 5/1986 | Bedi et al. | |
| 4,586,503 A | 5/1986 | Kirsch et al. | |
| 4,590,702 A * | 5/1986 | Chestnutt | 43/53.5 |
| 4,593,693 A | 6/1986 | Schenck | |
| 4,595,007 A | 6/1986 | Mericle | |
| 4,612,932 A | 9/1986 | Caspar et al. | |
| 4,622,970 A | 11/1986 | Wozniak | |
| 4,624,255 A | 11/1986 | Schenck et al. | |
| 4,637,380 A | 1/1987 | Orejola | |
| 4,641,652 A | 2/1987 | Hutterer et al. | |
| 4,665,906 A | 5/1987 | Jervis | |
| 4,665,917 A | 5/1987 | Clanton et al. | |
| 4,683,895 A | 8/1987 | Pohndorf | |
| 4,706,362 A | 11/1987 | Strausburg | |
| 4,719,917 A | 1/1988 | Barrows et al. | |
| 4,719,924 A | 1/1988 | Crittenden et al. | |
| 4,730,615 A | 3/1988 | Sutherland et al. | |
| 4,732,151 A | 3/1988 | Jones | |
| 4,809,695 A | 3/1989 | Gwathmey et al. | |
| 4,820,298 A | 4/1989 | Leveen et al. | |
| 4,844,318 A | 7/1989 | Kunreuther | |
| 4,873,975 A | 10/1989 | Walsh et al. | |
| 4,890,615 A | 1/1990 | Caspari et al. | |
| 4,896,668 A | 1/1990 | Popoff et al. | |
| 4,899,744 A | 2/1990 | Fujitsuka et al. | |
| 4,901,721 A | 2/1990 | Hakki | |
| 4,923,461 A | 5/1990 | Caspari et al. | |
| 4,924,866 A | 5/1990 | Yoon | |
| 4,926,860 A | 5/1990 | Stice et al. | |
| 4,929,240 A | 5/1990 | Kirsch et al. | |
| 4,930,674 A | 6/1990 | Barak | |
| 4,932,955 A | 6/1990 | Merz et al. | |
| 4,935,027 A * | 6/1990 | Yoon | 606/146 |
| 4,950,015 A | 8/1990 | Nejib et al. | |
| 4,950,283 A | 8/1990 | Dzubow et al. | |
| 4,950,285 A | 8/1990 | Wilk | |
| 4,957,498 A | 9/1990 | Caspari et al. | |
| 4,983,176 A | 1/1991 | Cushman et al. | |
| 4,990,152 A | 2/1991 | Yoon | |
| 4,991,567 A | 2/1991 | McCuen et al. | |
| 4,994,069 A | 2/1991 | Ritchart et al. | |
| 4,997,439 A | 3/1991 | Chen | |
| 5,002,562 A | 3/1991 | Oberlander | |
| 5,002,563 A | 3/1991 | Pyka et al. | |
| 5,007,920 A | 4/1991 | Torre | |
| 5,011,481 A | 4/1991 | Myers et al. | |
| 5,020,713 A | 6/1991 | Kunreuther | |
| 5,026,379 A | 6/1991 | Yoon | |
| 5,032,127 A | 7/1991 | Frazee et al. | |
| 5,035,692 A | 7/1991 | Lyon et al. | |
| 5,035,702 A | 7/1991 | Taheri | |
| 5,042,707 A | 8/1991 | Taheri | |
| 5,047,047 A | 9/1991 | Yoon | |
| 5,053,047 A | 10/1991 | Yoon | |
| 5,064,431 A | 11/1991 | Gilbertson et al. | |
| 5,074,874 A | 12/1991 | Yoon et al. | |
| 5,088,692 A * | 2/1992 | Weiler | 254/28 |
| 5,100,418 A | 3/1992 | Yoon | |
| 5,100,421 A | 3/1992 | Christoudias | |
| 5,104,407 A | 4/1992 | Lam et al. | |
| 5,119,983 A | 6/1992 | Green et al. | |
| 5,123,913 A | 6/1992 | Wilk et al. | |
| 5,127,413 A | 7/1992 | Ebert | |
| 5,129,913 A | 7/1992 | Ruppert | |
| 5,152,769 A | 10/1992 | Baber | |
| 5,154,189 A | 10/1992 | Oberlander | |
| 5,158,566 A | 10/1992 | Pianetti | |
| 5,171,250 A | 12/1992 | Yoon | |
| 5,171,252 A | 12/1992 | Friedland | |
| 5,174,087 A | 12/1992 | Bruno | |
| 5,178,634 A | 1/1993 | Ramos Martinez | |
| 5,192,294 A | 3/1993 | Blake, III | |
| 5,196,022 A | 3/1993 | Bilweis | |
| 5,201,880 A | 4/1993 | Wright et al. | |
| 5,207,694 A | 5/1993 | Broome | |
| 5,217,027 A | 6/1993 | Hermens | |
| 5,219,358 A * | 6/1993 | Bendel et al. | 606/222 |
| 5,221,259 A | 6/1993 | Weldon et al. | |
| 5,222,961 A | 6/1993 | Nakao et al. | |
| 5,222,976 A | 6/1993 | Yoon | |
| 5,234,447 A | 8/1993 | Kaster et al. | |
| 5,236,440 A | 8/1993 | Hlavacek | |
| 5,242,456 A | 9/1993 | Nash et al. | |
| 5,242,457 A | 9/1993 | Akopov et al. | |
| 5,246,443 A | 9/1993 | Mai | |
| 5,250,053 A | 10/1993 | Snyder | |
| 5,258,011 A | 11/1993 | Drews | |
| 5,261,917 A | 11/1993 | Hasson et al. | |
| 5,269,783 A | 12/1993 | Sander | |
| 5,269,809 A | 12/1993 | Hayhurst et al. | |
| 5,282,825 A | 2/1994 | Muck et al. | |
| 5,290,289 A | 3/1994 | Sanders et al. | |
| 5,304,117 A | 4/1994 | Wilk | |

| | | |
|---|---|---|
| 5,304,204 A | 4/1994 | Bregen |
| 5,306,296 A | 4/1994 | Wright et al. |
| 5,312,436 A | 5/1994 | Coffey et al. |
| 5,314,468 A | 5/1994 | Ramos Martinez |
| 5,330,503 A | 7/1994 | Yoon |
| 5,334,196 A | 8/1994 | Scott et al. |
| 5,336,233 A | 8/1994 | Chen |
| 5,336,239 A | 8/1994 | Gimpelson |
| 5,346,459 A | 9/1994 | Allen |
| 5,350,420 A | 9/1994 | Cosgrove et al. |
| 5,353,804 A | 10/1994 | Kornberg et al. |
| 5,355,897 A | 10/1994 | Pietrafitta et al. |
| 5,356,424 A | 10/1994 | Buzerak et al. |
| 5,364,406 A | 11/1994 | Sewell |
| 5,366,459 A | 11/1994 | Yoon |
| 5,366,462 A | 11/1994 | Kaster et al. |
| 5,366,479 A | 11/1994 | McGarry et al. |
| 5,374,268 A | 12/1994 | Sander |
| 5,376,096 A * | 12/1994 | Foster ............... 606/147 |
| 5,382,259 A | 1/1995 | Phelps et al. |
| 5,383,904 A | 1/1995 | Totakura et al. |
| 5,387,227 A * | 2/1995 | Grice ............... 606/222 |
| 5,403,331 A | 4/1995 | Chesterfield |
| 5,403,333 A | 4/1995 | Kaster et al. |
| 5,403,338 A | 4/1995 | Milo |
| 5,403,346 A | 4/1995 | Loeser |
| 5,413,584 A * | 5/1995 | Schulze ............... 606/219 |
| 5,417,684 A | 5/1995 | Jackson et al. |
| 5,417,700 A | 5/1995 | Egan |
| 5,423,821 A | 6/1995 | Pasque |
| 5,431,666 A | 7/1995 | Sauer et al. |
| 5,437,680 A | 8/1995 | Yoon |
| 5,437,681 A | 8/1995 | Meade et al. |
| 5,437,685 A | 8/1995 | Blasnik |
| 5,439,479 A | 8/1995 | Shichman et al. |
| 5,445,167 A | 8/1995 | Yoon et al. |
| 5,445,644 A | 8/1995 | Pietrafitta et al. |
| 5,450,860 A | 9/1995 | O'Connor |
| 5,451,231 A | 9/1995 | Rabenau et al. |
| 5,452,733 A | 9/1995 | Sterman et al. |
| 5,454,834 A | 10/1995 | Boebel et al. |
| 5,456,246 A | 10/1995 | Schmieding et al. |
| 5,462,561 A | 10/1995 | Voda |
| 5,474,557 A | 12/1995 | Mai |
| 5,480,405 A | 1/1996 | Yoon |
| 5,486,187 A | 1/1996 | Schenck |
| 5,486,197 A | 1/1996 | Le et al. |
| 5,488,958 A | 2/1996 | Topel et al. |
| 5,496,334 A | 3/1996 | Klundt et al. |
| 5,499,990 A | 3/1996 | Schulken et al. |
| 5,500,000 A | 3/1996 | Feagin et al. |
| 5,501,991 A | 3/1996 | Jang |
| 5,522,884 A | 6/1996 | Wright |
| 5,527,342 A | 6/1996 | Pietrzak et al. |
| 5,533,236 A | 7/1996 | Tseng |
| 5,538,509 A | 7/1996 | Dunlap et al. |
| 5,545,214 A | 8/1996 | Stevens |
| 5,549,619 A | 8/1996 | Peters et al. |
| 5,556,411 A | 9/1996 | Taoda et al. |
| 5,562,685 A | 10/1996 | Mollenauer et al. |
| 5,569,205 A | 10/1996 | Hart et al. |
| 5,569,274 A | 10/1996 | Rapacki et al. |
| 5,569,301 A | 10/1996 | Granger et al. |
| 5,571,119 A | 11/1996 | Atala |
| 5,571,175 A | 11/1996 | Vanney et al. |
| 5,582,616 A * | 12/1996 | Bolduc et al. ............... 606/143 |
| 5,582,619 A | 12/1996 | Ken |
| 5,584,879 A | 12/1996 | Reimold et al. |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,597,378 A | 1/1997 | Jervis |
| 5,601,571 A | 2/1997 | Moss |
| 5,601,572 A | 2/1997 | Middleman et al. |
| 5,601,600 A | 2/1997 | Ton |
| 5,603,718 A | 2/1997 | Xu |
| 5,609,608 A | 3/1997 | Benett et al. |
| 5,628,757 A | 5/1997 | Hasson |
| 5,630,540 A | 5/1997 | Blewett |
| 5,632,752 A | 5/1997 | Buelna |
| 5,632,753 A | 5/1997 | Loeser |
| 5,643,295 A | 7/1997 | Yoon |
| 5,643,305 A | 7/1997 | Al-Tameem |
| 5,645,568 A | 7/1997 | Chervitz et al. |
| 5,653,716 A * | 8/1997 | Malo et al. ............... 606/139 |
| 5,653,718 A | 8/1997 | Yoon |
| 5,658,312 A | 8/1997 | Green et al. |
| 5,660,186 A | 8/1997 | Bachir |
| 5,665,109 A | 9/1997 | Yoon |
| 5,669,918 A | 9/1997 | Balazs et al. |
| 5,676,670 A | 10/1997 | Kim |
| 5,683,417 A | 11/1997 | Cooper |
| 5,690,662 A | 11/1997 | Chiu et al. |
| 5,695,504 A | 12/1997 | Gifford, III et al. |
| 5,695,505 A | 12/1997 | Yoon |
| 5,697,913 A | 12/1997 | Sierocuk et al. |
| 5,697,943 A | 12/1997 | Sauer et al. |
| 5,700,270 A | 12/1997 | Peyser et al. |
| 5,700,271 A | 12/1997 | Whitfield et al. |
| 5,702,412 A | 12/1997 | Popov et al. |
| 5,707,362 A | 1/1998 | Yoon |
| 5,707,380 A | 1/1998 | Hinchliffe et al. |
| 5,709,693 A | 1/1998 | Taylor |
| 5,709,695 A | 1/1998 | Northrup, III |
| 5,715,987 A | 2/1998 | Kelley et al. |
| 5,720,755 A | 2/1998 | Dakov |
| 5,725,539 A | 3/1998 | Matern |
| 5,725,542 A | 3/1998 | Yoon |
| 5,728,135 A | 3/1998 | Bregen et al. |
| 5,732,872 A | 3/1998 | Bolduc et al. |
| 5,735,290 A | 4/1998 | Sterman et al. |
| 5,746,753 A * | 5/1998 | Sullivan et al. ............... 606/147 |
| 5,755,778 A | 5/1998 | Kleshinski |
| 5,766,189 A | 6/1998 | Matsuno |
| 5,769,870 A | 6/1998 | Salahich et al. |
| 5,779,718 A | 7/1998 | Green et al. |
| 5,782,397 A | 7/1998 | Koukline |
| 5,782,844 A | 7/1998 | Yoon et al. |
| 5,797,920 A | 8/1998 | Kim |
| 5,797,933 A | 8/1998 | Snow et al. |
| 5,797,934 A | 8/1998 | Rygaard |
| 5,797,960 A | 8/1998 | Stevens et al. |
| 5,799,661 A | 9/1998 | Boyd et al. |
| 5,799,857 A | 9/1998 | Robertson et al. |
| 5,810,848 A | 9/1998 | Hayhurst |
| 5,810,851 A | 9/1998 | Yoon |
| 5,810,853 A | 9/1998 | Yoon |
| 5,810,882 A | 9/1998 | Bolduc et al. |
| 5,817,113 A | 10/1998 | Gifford, III et al. |
| 5,820,631 A | 10/1998 | Nobles |
| 5,824,002 A | 10/1998 | Gentelia et al. |
| 5,824,008 A | 10/1998 | Bolduc et al. |
| 5,827,265 A | 10/1998 | Glinsky et al. |
| 5,827,316 A | 10/1998 | Young et al. |
| 5,830,221 A | 11/1998 | Stein et al. |
| 5,830,222 A | 11/1998 | Makower |
| 5,833,698 A | 11/1998 | Hinchliffe |
| 5,849,019 A | 12/1998 | Yoon |
| 5,851,216 A | 12/1998 | Allen |
| 5,855,614 A | 1/1999 | Stevens et al. |
| 5,868,702 A | 2/1999 | Stevens et al. |
| 5,868,763 A | 2/1999 | Spence et al. |
| 5,871,528 A | 2/1999 | Camps et al. |
| 5,879,371 A | 3/1999 | Gardiner et al. |
| 5,881,943 A | 3/1999 | Heck et al. |
| 5,882,340 A | 3/1999 | Yoon |
| 5,891,130 A | 4/1999 | Palermo et al. |
| 5,891,160 A | 4/1999 | Williamson, IV et al. |
| 5,893,369 A | 4/1999 | LeMole |
| 5,893,865 A | 4/1999 | Swindle et al. |
| 5,893,886 A | 4/1999 | Zegdi et al. |
| 5,895,394 A | 4/1999 | Kienzle et al. |
| 5,904,697 A | 5/1999 | Gifford, III et al. |
| 5,908,428 A | 6/1999 | Scirica et al. |
| 5,911,352 A | 6/1999 | Racenet et al. |
| 5,919,207 A | 7/1999 | Taheri |
| 5,931,842 A | 8/1999 | Goldsteen et al. |

| Patent | Kind | Date | Inventor |
|---|---|---|---|
| 5,941,434 | A | 8/1999 | Green |
| 5,941,442 | A | 8/1999 | Geiste et al. |
| 5,941,888 | A | 8/1999 | Wallace et al. |
| 5,941,908 | A | 8/1999 | Goldsteen et al. |
| 5,944,730 | A | 8/1999 | Nobles et al. |
| 5,951,576 | A | 9/1999 | Wakabayashi |
| 5,951,600 | A | 9/1999 | Lemelson |
| 5,954,735 | A | 9/1999 | Rygaard |
| 5,957,363 | A | 9/1999 | Heck |
| 5,957,938 | A | 9/1999 | Zhu et al. |
| 5,957,940 | A | 9/1999 | Tanner et al. |
| 5,961,481 | A | 10/1999 | Sterman et al. |
| 5,961,539 | A | 10/1999 | Northrup, III et al. |
| 5,964,772 | A | 10/1999 | Bolduc et al. |
| 5,964,782 | A | 10/1999 | Lafontaine et al. |
| 5,972,024 | A | 10/1999 | Northrup, III et al. |
| 5,976,159 | A | 11/1999 | Bolduc et al. |
| 5,976,161 | A | 11/1999 | Kirsch et al. |
| 5,976,164 | A | 11/1999 | Bencini et al. |
| 5,976,178 | A | 11/1999 | Goldsteen et al. |
| 5,984,917 | A | 11/1999 | Fleischman et al. |
| 5,984,959 | A | 11/1999 | Robertson et al. |
| 5,989,242 | A | 11/1999 | Saadat et al. |
| 5,989,268 | A | 11/1999 | Pugsley, Jr. et al. |
| 5,989,276 | A | 11/1999 | Houser et al. |
| 5,989,278 | A | 11/1999 | Mueller |
| 5,993,468 | A | 11/1999 | Rygaard |
| 5,997,556 | A | 12/1999 | Tanner |
| 6,001,110 | A | 12/1999 | Adams |
| 6,007,544 | A | 12/1999 | Kim |
| 6,010,531 | A | 1/2000 | Donlon et al. |
| 6,013,084 | A | 1/2000 | Ken et al. |
| 6,022,367 | A | 2/2000 | Sherts |
| 6,024,748 | A | 2/2000 | Manzo et al. |
| 6,032,849 | A | 3/2000 | Mastri et al. |
| 6,033,419 | A | 3/2000 | Hamblin, Jr. et al. |
| 6,036,699 | A | 3/2000 | Andreas et al. |
| 6,036,703 | A | 3/2000 | Evans et al. |
| 6,036,710 | A | 3/2000 | McGarry et al. |
| 6,042,607 | A | 3/2000 | Williamson et al. |
| 6,056,751 | A | 5/2000 | Fenton |
| 6,063,070 | A | 5/2000 | Eder |
| 6,066,148 | A | 5/2000 | Rygaard |
| 6,074,401 | A | 6/2000 | Gardiner et al. |
| 6,074,418 | A | 6/2000 | Buchanan et al. |
| 6,077,291 | A | 6/2000 | Das |
| 6,080,114 | A | 6/2000 | Russin |
| 6,083,237 | A | 7/2000 | Huitema et al. |
| 6,106,538 | A | 8/2000 | Shiber |
| 6,110,188 | A | 8/2000 | Narciso |
| 6,113,611 | A | 9/2000 | Allen et al. |
| 6,113,612 | A | 9/2000 | Swanson et al. |
| 6,120,524 | A | 9/2000 | Taheri |
| 6,132,438 | A | 10/2000 | Fleischman et al. |
| 6,139,540 | A | 10/2000 | Rost et al. |
| 6,143,004 | A | 11/2000 | Davis et al. |
| 6,149,658 | A | 11/2000 | Gardiner et al. |
| 6,152,935 | A | 11/2000 | Kammerer et al. |
| 6,152,937 | A | 11/2000 | Peterson et al. |
| 6,159,165 | A | 12/2000 | Ferrera et al. |
| 6,159,225 | A | 12/2000 | Makower |
| 6,165,183 | A | 12/2000 | Kuehn et al. |
| 6,165,185 | A | 12/2000 | Shennib et al. |
| 6,171,320 | B1 | 1/2001 | Monassevitch |
| 6,171,321 | B1 | 1/2001 | Gifford, III et al. |
| 6,176,413 | B1 | 1/2001 | Heck et al. |
| 6,176,864 | B1 | 1/2001 | Chapman |
| 6,179,840 | B1 | 1/2001 | Bowman |
| 6,179,848 | B1 | 1/2001 | Solem |
| 6,179,849 | B1 | 1/2001 | Yencho et al. |
| 6,183,512 | B1 | 2/2001 | Howanec et al. |
| 6,190,373 | B1 | 2/2001 | Palermo et al. |
| 6,193,733 | B1 | 2/2001 | Adams |
| 6,193,734 | B1 | 2/2001 | Bolduc et al. |
| 6,197,037 | B1 | 3/2001 | Hair |
| 6,217,611 | B1 | 4/2001 | Klostermeyer |
| 6,221,083 | B1 | 4/2001 | Mayer |
| 6,241,738 | B1 | 6/2001 | Dereume |
| 6,241,741 | B1 | 6/2001 | Duhaylongsod et al. |
| 6,248,117 | B1 | 6/2001 | Blatter |
| 6,250,308 | B1 | 6/2001 | Cox |
| 6,254,615 | B1 | 7/2001 | Bolduc et al. |
| 6,269,819 | B1 | 8/2001 | Oz et al. |
| 6,280,460 | B1 | 8/2001 | Bolduc et al. |
| 6,283,979 | B1 | 9/2001 | Mers Kelly et al. |
| 6,283,993 | B1 | 9/2001 | Cosgrove et al. |
| 6,296,622 | B1 | 10/2001 | Kurz et al. |
| 6,296,656 | B1 | 10/2001 | Bolduc et al. |
| 6,306,141 | B1 | 10/2001 | Jervis |
| 6,332,893 | B1 | 12/2001 | Mortier et al. |
| 6,346,074 | B1 | 2/2002 | Roth |
| 6,346,112 | B2 | 2/2002 | Adams |
| 6,350,269 | B1 | 2/2002 | Shipp et al. |
| 6,352,543 | B1 | 3/2002 | Cole |
| 6,358,258 | B1 | 3/2002 | Arcia et al. |
| 6,361,559 | B1 | 3/2002 | Houser et al. |
| 6,368,348 | B1 | 4/2002 | Gabbay |
| 6,371,964 | B1 | 4/2002 | Vargas et al. |
| 6,387,105 | B1 | 5/2002 | Gifford, III et al. |
| 6,391,038 | B2 | 5/2002 | Vargas et al. |
| 6,402,764 | B1 | 6/2002 | Hendricksen et al. |
| 6,406,492 | B1 | 6/2002 | Lytle |
| 6,406,493 | B1 | 6/2002 | Tu et al. |
| 6,409,739 | B1 | 6/2002 | Nobles et al. |
| 6,409,758 | B2 | 6/2002 | Stobie et al. |
| 6,416,527 | B1 | 7/2002 | Berg et al. |
| 6,418,597 | B1 | 7/2002 | Deschenes et al. |
| 6,419,658 | B1 | 7/2002 | Restelli et al. |
| 6,419,681 | B1 | 7/2002 | Vargas et al. |
| 6,419,695 | B1 | 7/2002 | Gabbay |
| 6,425,900 | B1 | 7/2002 | Knodel et al. |
| 6,428,550 | B1 | 8/2002 | Vargas et al. |
| 6,428,555 | B1 | 8/2002 | Koster, Jr. |
| 6,451,048 | B1 | 9/2002 | Berg et al. |
| 6,461,320 | B1 | 10/2002 | Yencho et al. |
| 6,475,222 | B1 | 11/2002 | Berg et al. |
| 6,478,804 | B2 | 11/2002 | Vargas et al. |
| 6,485,496 | B1 | 11/2002 | Suyker et al. |
| 6,491,707 | B2 | 12/2002 | Makower et al. |
| 6,497,671 | B2 | 12/2002 | Ferrera et al. |
| 6,497,710 | B2 | 12/2002 | Yencho et al. |
| 6,514,265 | B2 | 2/2003 | Ho et al. |
| 6,517,558 | B2 | 2/2003 | Gittings et al. |
| 6,524,338 | B1 | 2/2003 | Gundry |
| 6,533,812 | B2 | 3/2003 | Swanson et al. |
| 6,537,288 | B2 | 3/2003 | Vargas et al. |
| 6,547,799 | B2 | 4/2003 | Hess et al. |
| 6,551,332 | B1 | 4/2003 | Nguyen et al. |
| 6,562,053 | B2 | 5/2003 | Schulze et al. |
| 6,575,985 | B2 | 6/2003 | Knight et al. |
| 6,589,255 | B2 | 7/2003 | Schulze et al. |
| 6,607,541 | B1 | 8/2003 | Gardiner et al. |
| 6,607,542 | B1 | 8/2003 | Wild |
| 6,613,059 | B2 | 9/2003 | Schaller et al. |
| 6,629,988 | B2 | 10/2003 | Weadock |
| 6,635,214 | B2 | 10/2003 | Rapacki et al. |
| 6,641,593 | B1 | 11/2003 | Schaller et al. |
| 6,648,900 | B2 | 11/2003 | Fleischman et al. |
| 6,651,670 | B2 | 11/2003 | Rapacki et al. |
| 6,651,672 | B2 | 11/2003 | Roth |
| 6,652,540 | B1 | 11/2003 | Cole et al. |
| 6,652,541 | B1 | 11/2003 | Vargas et al. |
| 6,660,015 | B1 | 12/2003 | Berg et al. |
| 6,682,540 | B1 | 1/2004 | Sancoff et al. |
| 6,695,859 | B1 | 2/2004 | Golden et al. |
| 6,702,826 | B2 | 3/2004 | Liddicoat et al. |
| 6,709,442 | B2 | 3/2004 | Miller et al. |
| 6,712,829 | B2 | 3/2004 | Schulze |
| 6,719,768 | B1 | 4/2004 | Cole et al. |
| 6,743,243 | B1 | 6/2004 | Roy et al. |
| 6,749,622 | B2 | 6/2004 | McGuckin et al. |
| 6,776,782 | B2 | 8/2004 | Schulze |
| 6,776,784 | B2 | 8/2004 | Ginn |
| 6,776,785 | B2 | 8/2004 | Yencho et al. |
| 6,802,847 | B1 | 10/2004 | Carson et al. |
| 6,821,286 | B1 | 11/2004 | Carranza et al. |
| 6,869,444 | B2 | 3/2005 | Gabbay |
| 6,913,607 | B2 | 7/2005 | Ainsworth et al. |

| | | | | | |
|---|---|---|---|---|---|
| 6,918,917 B1 | 7/2005 | Nguyen et al. | EP | 0419597 | 4/1991 |
| 6,921,407 B2 | 7/2005 | Nguyen et al. | EP | 0432692 | 6/1991 |
| 6,926,730 B1 | 8/2005 | Nguyen et al. | EP | 0494636 | 7/1992 |
| 6,945,980 B2 | 9/2005 | Nguyen et al. | EP | 0537955 | 4/1993 |
| 6,955,679 B1 | 10/2005 | Hendricksen et al. | EP | 0559429 | 9/1993 |
| 6,960,221 B2 | 11/2005 | Ho et al. | EP | 0598529 | 5/1994 |
| 6,979,337 B2 | 12/2005 | Kato | EP | 0632999 | 1/1995 |
| 6,979,338 B1 | 12/2005 | Loshakove et al. | EP | 0641546 | 3/1995 |
| 7,022,131 B1 | 4/2006 | Derowe et al. | EP | 0656191 | 6/1995 |
| 7,056,330 B2 | 6/2006 | Gayton | EP | 0687446 | 12/1995 |
| 7,063,711 B1 | 6/2006 | Loshakove et al. | EP | 0705568 | 4/1996 |
| 7,070,618 B2 | 7/2006 | Streeter | EP | 0711532 | 5/1996 |
| 7,182,769 B2 | 2/2007 | Ainsworth et al. | EP | 0705569 | 10/1996 |
| 7,220,268 B2 | 5/2007 | Blatter | EP | 0734697 | 10/1996 |
| 2001/0018592 A1 | 8/2001 | Schaller et al. | EP | 0478949 | 3/1997 |
| 2001/0018593 A1 | 8/2001 | Nguyen et al. | EP | 0778005 | 6/1997 |
| 2001/0018611 A1 | 8/2001 | Solem et al. | EP | 0815795 | 1/1998 |
| 2001/0021856 A1 | 9/2001 | Bolduc et al. | GB | 2223410 | 4/1990 |
| 2001/0047181 A1 | 11/2001 | Ho et al. | JP | 07308322 | 11/1995 |
| 2002/0010490 A1 | 1/2002 | Schaller et al. | JP | 08336544 | 12/1996 |
| 2002/0042623 A1 | 4/2002 | Blatter et al. | JP | 10337291 | 12/1998 |
| 2002/0082614 A1 | 6/2002 | Logan et al. | RU | 2110222 | 5/1998 |
| 2002/0099395 A1 | 7/2002 | Acampora et al. | SU | 577022 | 10/1977 |
| 2002/0151916 A1 | 10/2002 | Muramatsu et al. | SU | 1186199 | 10/1985 |
| 2002/0165561 A1 | 11/2002 | Ainsworth et al. | SU | 1456109 | 2/1989 |
| 2002/0173803 A1 | 11/2002 | Yang et al. | SU | 1560133 | 4/1990 |
| 2003/0074012 A1 | 4/2003 | Nguyen et al. | WO | WO 90/06725 | 6/1990 |
| 2003/0078603 A1 | 4/2003 | Schaller et al. | WO | WO 90/09149 | 8/1990 |
| 2003/0083742 A1 | 5/2003 | Spence et al. | WO | WO 90/14795 | 12/1990 |
| 2003/0093118 A1 | 5/2003 | Ho et al. | WO | 91/08708 | 6/1991 |
| 2003/0125755 A1 | 7/2003 | Schaller et al. | WO | WO 91/07916 | 6/1991 |
| 2003/0191481 A1 | 10/2003 | Nguyen et al. | WO | WO 91/17712 | 11/1991 |
| 2003/0195531 A1 | 10/2003 | Nguyen et al. | WO | WO 92/05828 | 4/1992 |
| 2003/0199974 A1 | 10/2003 | Lee et al. | WO | 92/12676 | 8/1992 |
| 2004/0050393 A1 | 3/2004 | Golden et al. | WO | 92/22041 | 12/1992 |
| 2004/0068276 A1 | 4/2004 | Golden et al. | WO | 93/01750 | 2/1993 |
| 2004/0102797 A1 | 5/2004 | Golden et al. | WO | 94/15535 | 7/1994 |
| 2004/0111099 A1 | 6/2004 | Nguyen et al. | WO | WO 94/15537 | 7/1994 |
| 2004/0138685 A1 | 7/2004 | Clague et al. | WO | WO 96/00035 | 1/1996 |
| 2004/0176663 A1 | 9/2004 | Edoga | WO | WO 96/06565 | 3/1996 |
| 2004/0193259 A1 | 9/2004 | Gabbay | WO | WO 96/38090 | 12/1996 |
| 2005/0004582 A1 | 1/2005 | Edoga | WO | 97/12555 | 4/1997 |
| 2005/0021054 A1 | 1/2005 | Ainsworth et al. | WO | 97/16122 | 5/1997 |
| 2005/0043749 A1 | 2/2005 | Breton et al. | WO | 97/27898 | 8/1997 |
| 2005/0065601 A1 | 3/2005 | Lee et al. | WO | WO 97/28744 | 8/1997 |
| 2005/0070924 A1 | 3/2005 | Schaller et al. | WO | 97/31575 | 9/1997 |
| 2005/0075659 A1 | 4/2005 | Realyvasquez et al. | WO | WO 97/32526 | 9/1997 |
| 2005/0075667 A1 | 4/2005 | Schaller et al. | WO | 97/40754 | 11/1997 |
| 2005/0080454 A1 | 4/2005 | Drews | WO | WO 97/42881 | 11/1997 |
| 2005/0101975 A1 | 5/2005 | Nguyen et al. | WO | 98/19636 | 5/1998 |
| 2005/0107871 A1 | 5/2005 | Realyvasquez et al. | WO | 98/30153 | 7/1998 |
| 2005/0131429 A1 | 6/2005 | Ho et al. | WO | 98/42262 | 10/1998 |
| 2005/0267572 A1 | 12/2005 | Schoon et al. | WO | 98/48707 | 11/1998 |
| 2006/0004389 A1 | 1/2006 | Nguyen et al. | WO | 98/52475 | 11/1998 |
| 2006/0253143 A1 | 11/2006 | Edoga | WO | 99/07294 | 2/1999 |
| 2006/0271081 A1 | 11/2006 | Realyvasquez | WO | 99/12484 | 3/1999 |
| 2006/0293701 A1 | 12/2006 | Ainsworth et al. | WO | 99/15088 | 4/1999 |
| 2007/0010835 A1 | 1/2007 | Breton et al. | WO | 99/37218 | 7/1999 |
| 2007/0027461 A1 | 2/2007 | Gardiner et al. | WO | 99/62408 | 12/1999 |
| 2007/0106313 A1 | 5/2007 | Golden et al. | WO | 99/62415 | 12/1999 |
| 2007/0142848 A1 | 6/2007 | Ainsworth et al. | WO | 99/63910 | 12/1999 |
| | | | WO | 99/65409 | 12/1999 |
| FOREIGN PATENT DOCUMENTS | | | WO | WO 99/62406 A2 | 12/1999 |
| DE | 2703529 | 8/1978 | WO | WO 99/62409 A1 | 12/1999 |
| DE | 3203410 | 11/1982 | WO | 00/03759 | 1/2000 |
| DE | 3227984 | 2/1984 | WO | 00/15144 | 3/2000 |
| DE | 3504202 | 8/1985 | WO | 00/59380 | 10/2000 |
| DE | 4133800 | 1/1993 | WO | 00/60995 | 10/2000 |
| DE | 4402058 | 4/1995 | WO | 00/64381 | 11/2000 |
| DE | 19547617 | 9/1997 | WO | 00/74603 | 12/2000 |
| DE | 19732234 | 1/1999 | WO | 01/19292 | 3/2001 |
| EP | 0072232 | 2/1983 | WO | 01/26557 | 4/2001 |
| EP | 0122046 | 3/1983 | WO | 01/26586 | 4/2001 |
| EP | 0121362 | 10/1984 | WO | 01/28432 | 4/2001 |
| EP | 0129441 | 12/1984 | WO | 01/54618 | 8/2001 |
| EP | 0130037 | 1/1985 | WO | 01/74254 | 10/2001 |
| EP | 0140557 | 5/1985 | WO | 02/13701 | 2/2002 |
| EP | 0326426 | 8/1989 | WO | 02/13702 | 2/2002 |
| EP | 0409569 | 1/1991 | WO | 02/30295 | 4/2002 |

| | | |
|---|---|---|
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2005/011468 | 2/2005 |
| WO | 2005/058170 | 6/2005 |

OTHER PUBLICATIONS

Written Opinion PCT/US00/24056 Jul. 13, 2001.
International Search Report PCT/US00/24056, Nov. 8, 2000.
International Preliminary Examination Report PCT/US00/24056, Jan. 3, 2002.
US 6,503,260, 1/2003, Schaller et al. (withdrawn).
"VCS Clip Applier System," published in 1995 by Auto Suture Company, a Division of U.S. Surgical Corporation.
Chitwood Jr., Mitral Valve Repair: Ischemic, Mastery of Cardiothoracic Surgery, Lippencott-Raven Publishers, 1998, Chapter 32, pp. 309-321.
Grondin, et al., Carpentier's Annulus and De Vega's Annuloplasty: The end of the tricuspid challenge, Nov. 1975, vol. 70, pp. 852-861.
Holper, et al., Surgery for Tricuspid Insufficiency: Long Term Follow-Up After De Vega Annuloplasty, Thorac Cardiovasc Surgeon, 41, 1993.
Maisano, et al., The Double Orifice Technique as a Standardized Approach to Treat Mitral Regurgitation Due to Severe Myxomatous Disease: Surgical Technique, European Journal of Cardiothoracic Surgery, vol. 17, 2000, 201-205.
Rabago, et al., The New De Vega Technique In Tricuspid Annuloplasty: Results in 150 patients, J. Cardiovas Surg. 1980, 21 pp. 231-238.
Rivera, et al., Carpentier's Flexible Ring Versus De Vega's Annuloplasty, J Thorac Cardiovas Surg, Feb. 1985, 89 pp. 196-203.
Wei, et al., De Vega's Semicircular Annuloplasty for Tricuspid Valve Regurgitation, Ann Thorac Surg, 1993, 55: pp. 482-485.
Wylie, et al., Manual of Vascular Surgery, R. H. Egdahl ed. Spring-Verlag: New York, vol. II, 1986, Table of Contents only.
Wylie, et al., Manual of Vascular Surgery, Springer-Verlag New York, vol. I, 1980, Table of Contents only.
Yun, et al. Mitral Valve Replacement, Mastery of Cardiothoracic Surgery, Lippencott-Raven Publishers, 1998, Chapter 34, pp. 329-341.
International Search Report PCT/US98/00462, 1998.
International Search Report PCT/US98/00795, 1998.
International Search Report PCT/US98/14211, 1998.
International Search Report PCT/US99/12563, 1999.
International Search Report PCT/US99/12566, 1999.
International Search Report PCT/US00/09092, 2000.
International Search Report PCT/US01/10501, 2001.
International Search Report PCT/US01/31709, 2001.
International Search Report PCT/US01/42653, 2001.
International Search Report PCT/US02/10865, 2002.
International Search Report PCT/US02/10866, 2002.
International Search Report PCT/US02/14261, 2002.
International Search Report PCT/US03/12073, 2003.
International Preliminary Examination Report PCT/US98/00462, 1998.
International Preliminary Examination Report PCT/US98/00795, 1998.
International Preliminary Examination Report PCT/US99/12566 1999.
International Preliminary Examination Report PCT/US00/09092 2000.
International Preliminary Examination Report PCT/US01/31709 2001.
International Preliminary Examination Report PCT/US01/42653 2001.
International Preliminary Examination Report PCT/US02/14261 2002.
International Preliminary Examination Report PCT/US02/10865 2002.
International Preliminary Examination Report PCT/US02/10866 2002.
International Preliminary Examination Report PCT/US03/12073 2003.
Written Opinion PCT/US99/12563, 1999.
Written Opinion PCT/US99/12566, 1999.
Written Opinion PCT/US00/09092, 2000.
Written Opinion PCT/US01/10501, 2001.
Written Opinion PCT/US01/31709, 2001.
Written Opinion PCT/US02/10866, 2002.
Written Opinion PCT/US02/14261, 2002.
Written Opinion PCT/US03/12073, 2003.
International Preliminary Report on Patentability PCT/US2004/023728, 2004.

* cited by examiner

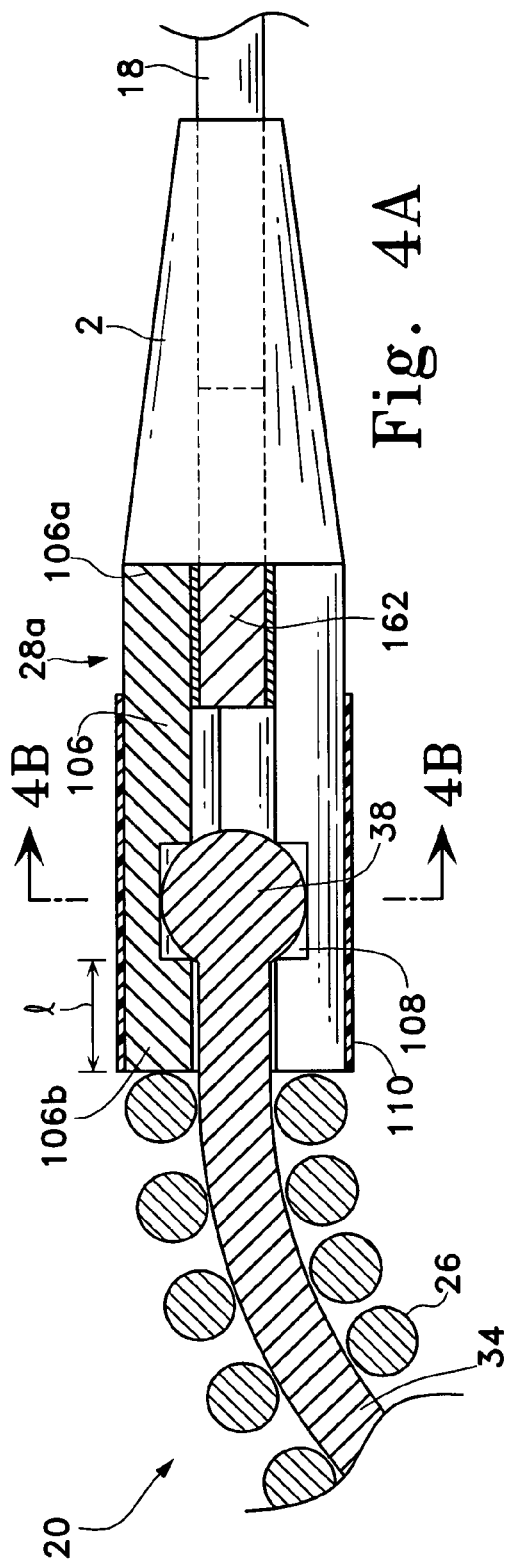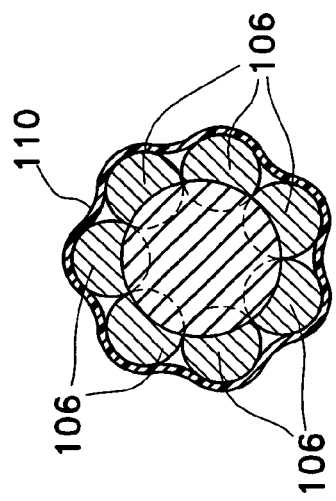
Fig. 4A
Fig. 4B

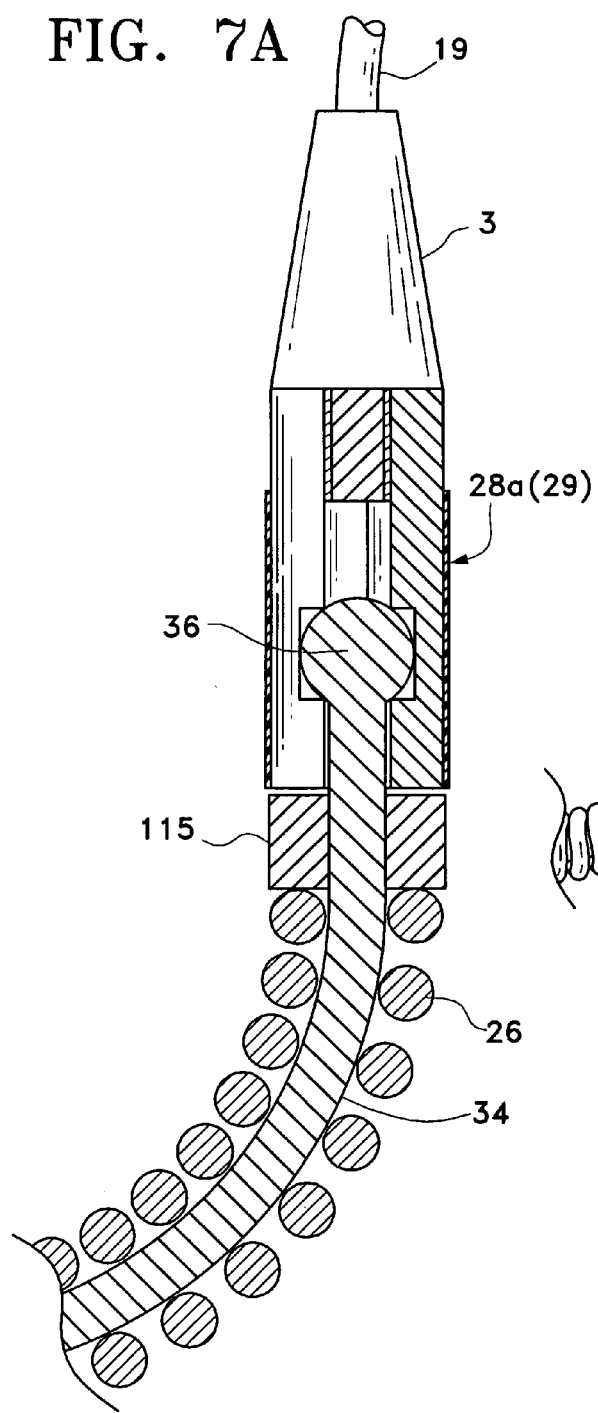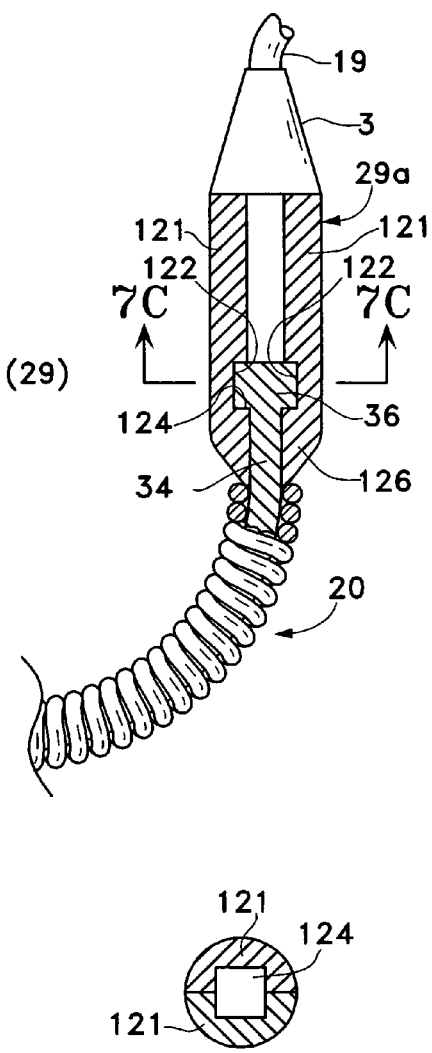
FIG. 7A FIG. 7B FIG. 7C

SURGICAL CLIP REMOVAL APPARATUS This application claims priority to provisional application Ser. No. 60/152,401 filed on Sep. 3, 1999, and also hereby incorporates by reference, the entirety thereof herein.

FIELD OF THE INVENTION

The present invention relates to instruments and methods for removing surgical fasteners for connecting body tissues, tissue and prostheses, tissue and graft or any combination thereof.

BACKGROUND OF THE INVENTION

Surgical fasteners have been used to connect various combinations of tissue, prostheses and graft materials. For example, fasteners have been used to connect tissue and graft in vascular anastomoses in conventional or minimally invasive procedure.

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar is delivered into the body with a cannula. After the trocar pierces into the body cavity, it is removed and the cannula is left with one end in the body cavity.

When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulae. When manipulating instruments through cannulae, it is extremely difficult to position tissues in their proper alignment with respect to each other, pass a needle through the tissues, form a knot with the suture material once the tissues are aligned, and prevent the suture material from becoming tangled.

The fastening of body tissues together, or of fastening body tissues to graft materials becomes much more difficult in the restricted spaces imposed upon a surgeon when working though cannulae. Because the use of sutures is often difficult if not impossible in these situations, various other forms of fasteners have been developed to simplify the joining together of tissues and tissues with grafts in these environments, as well as in more conventional surgical procedures.

PCT publication nos. WO 99/62406 and WO 99/62409, which are commonly assigned to the assignee of the present application, disclose tissue connector assemblies having a clip movable between an open state and a closed state and a mechanical restraining device attached to the clip for restraining the clip in its open state. The clip has a generally U-shaped configuration when in its open state. A needle may be releasably attached to the clip. This type of tissue connector assembly is discussed further below and in PCT publication nos. WO 99/62406 and WO 99/62409, which are incorporated herein, by reference thereto, in their entireties.

In some cases, as with sutures, however, the surgeon may find that the placement of a particular fastener is undesirable. Fasteners so deployed have been removed by simply cutting, as done with sutures. However, this may be difficult depending on the size and material of the fastener. Cutting may be especially difficult when the fastener is metal. In addition, cutting may cause a portion of the fastener to break down into small fragments which can then enter the bloodstream. Therefore, there is a need for a surgical fastener removal system that can easily and reliably remove a fastener after it has been deployed.

SUMMARY OF THE INVENTION

The present invention involves apparatus and methods for removing surgical fasteners. The apparatus includes a mechanism for opening a fastener so that it may be removed from, for example, tissue, prostheses or graft material, while minimizing the possibility of fracturing the fastener.

According to one embodiment, the apparatus includes a member adapted to grab the fastener. The member is slidably mounted in a housing configured such that after the fastener is grabbed with the member, the member can be drawn into the housing to open or straighten the fastener, thereby assisting in its removal.

According to another embodiment, a pair of grooved/beveled heads are arranged so that they may be brought into engagement with a portion of the fastener to place a force onto the constraint and thereby open or straighten the fastener, or place a straightening force on the fastener. For example, the fastener may comprise a shape memory wire having a generally loop shaped memory configuration and a coil surrounding the wire as described in PCT publication nos. WO 99/62406 and WO 99/62409 where the wire straightens when the coil is longitudinally compressed. The heads of the present invention are configured so that when placed or wedged between coil turns to compress a portion of the coil and urge the wire toward an open or straight configuration so that it can be readily removed.

BRIEF DESCRIPTION OF THE DRAWINGS

FIGS. 4A and 4B are sectional views of a fastener release mechanism, which may be used in the assembly of FIG. 3.

FIG. 7A shows a release mechanism that may be used with the second needle in the assembly of FIG. 6.

FIGS. 7B and 7C show another release mechanism that may be used with the second needle in the assembly of FIG. 6, where FIG. 7C is a sectional view of FIG. 7B taken along line 7C-7C.

FIGS. 7D and 7E are partial sectional views of the system in a coupled and decoupled state, respectfully.

FIGS. 8A and 8B are sectional views and FIG. 8C is a top view of the elongated grabber member of FIGS. 8A and 8B.

DESCRIPTION OF THE INVENTION

Figure 1:
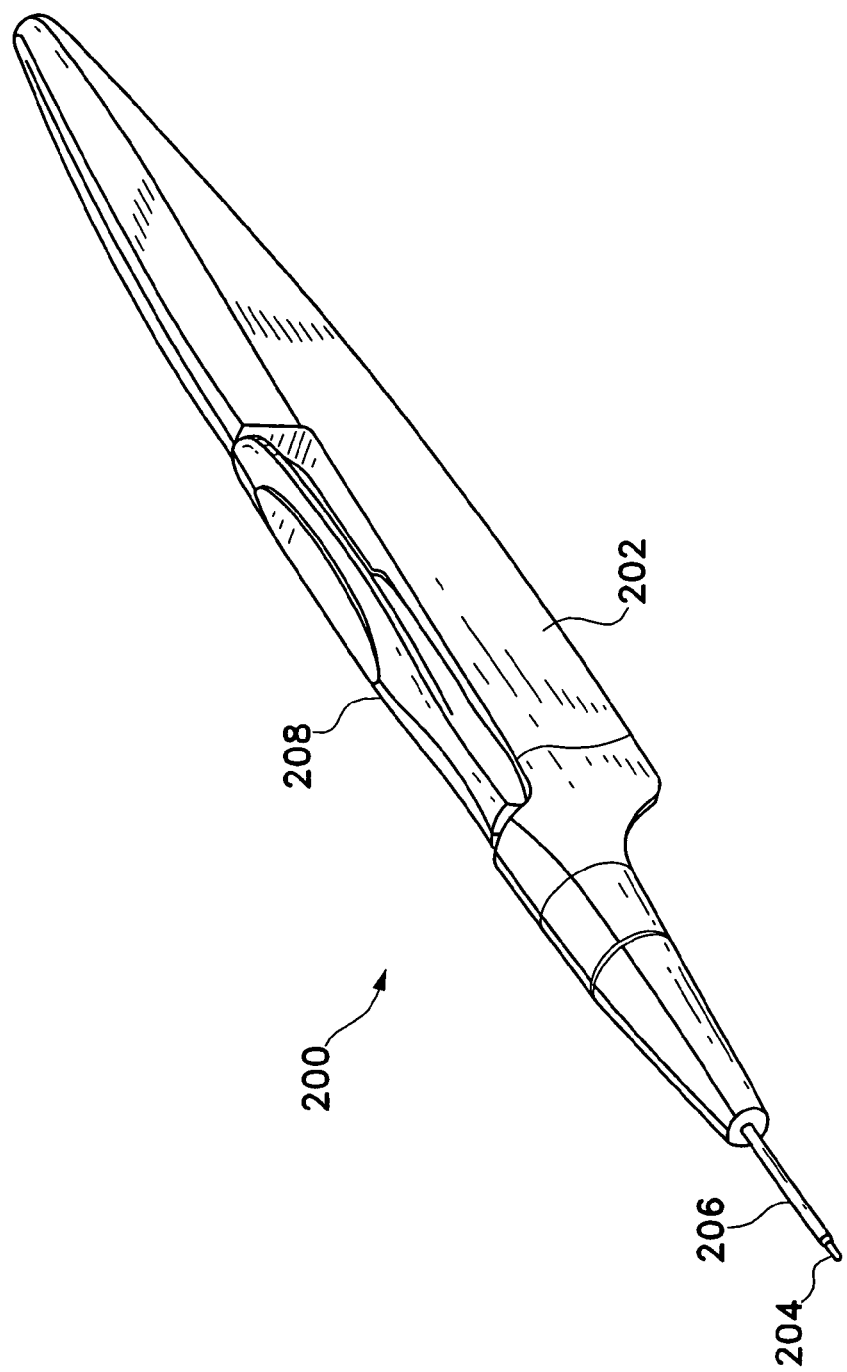
FIG. 1 is a perspective view of fastener removing apparatus in accordance with the principles of the present invention.

Referring to FIG. 1, one embodiment of a fastener removing apparatus is shown in accordance with the principles of the present invention. The fastener removing apparatus is generally designated with reference numeral 200 and includes a handle 202, a fastener grabber 204, a housing 206 for the grabber and an acutator 208 for moving the grabber relative to the housing so that it may extend therefrom or be positioned therein. Before describing the fastener removing apparatus in further detail, an exemplary group of fasteners, which can be removed with the apparatus, will be described. Although particular fasteners will be described below, it should be understood that the removing apparatus of the present invention may be used to remove other fasteners as well. For example, the removal apparatus may be used with any of the tissue connectors described in PCT publication nos. WO 99/62406 and WO 99/62409, referred to above.

Figure 2A:
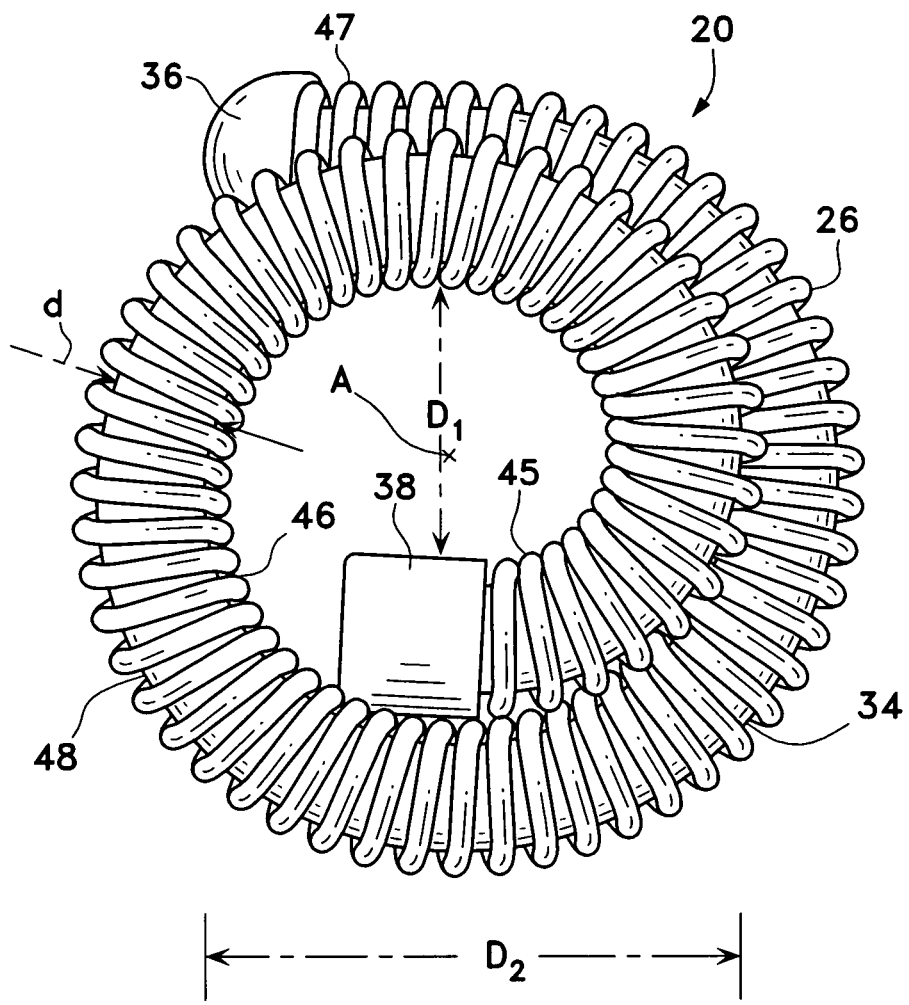
FIG. 2A is a plan view of a fastener, which may be manipulated with the apparatus of FIG. 1.

Referring to FIG. 2A, one embodiment of a fastener (e.g., fastener 20) comprises a deformable wire 34 made of a shape memory alloy. A nickel titanium (nitinol) based alloy may be used, for example. The nitinol may include additional elements which affect the yield strength of the material or the temperature at which particular pseudoelastic or shape transformation characteristics occur. The transformation temperature may be defined as the temperature at which a shape memory alloy finishes transforming from martensite to austenite upon heating (i.e., $A_f$ temperature). The shape memory alloy preferably exhibits pseudoelastic (superelastic) behavior when deformed at a temperature slightly above its transformation temperature. At least a portion of the shape memory alloy is converted from its austenitic phase to its martensitic phase when the wire is in its deformed configuration. As the stress is removed, the material undergoes a martensitic to austenitic conversion and springs back to its original undeformed configuration. When the wire is positioned within the tissue in its undeformed configuration, a residual stress is present to maintain the tissue tightly together. In order for the pseudoelastic wire to retain sufficient compression force in its undeformed configuration, the wire should not be stressed past its yield point in its deformed configuration to allow complete recovery of the wire to its undeformed configuration. The shape memory alloy is preferably selected with a transformation temperature suitable for use with a stopped heart condition where cold cardioplegia has been injected for temporary paralysis of the heart tissue (e.g., temperatures as low as 8-10 degrees Celsius).

It is to be understood that the shape memory alloy may also be heat activated, or a combination of heat activation and pseudoelastic properties may be used, as is known by those skilled in the art.

The cross-sectional diameter of the wire and length of the wire will vary depending on the specific application. The diameter "d" of wire 34 may be, for example, between 0.001 and 0.015 inch. For coronary bypass applications, the diameter is preferably between 0.001 and 0.008 inch with a diameter $D_1$ of the loop (FIG. 2A) being between 0.0125 and 0.0875 inch. The wire 34 may have a circular cross-sectional shape and a generally spiral shaped configuration when in a closed position as shown in FIG. 2A. The diameter $D_1$ of the loop of the fastener 20 (with coil 26, which may be platinum) in its closed position is preferably sized to prevent movement between adjacent tissues. It is to be understood, however, that the wire may have other cross-sectional shapes such as rectangular, or may have other constructions, (e.g., the wire may be formed from multiple strands).

One end of wire 34, may include an enlarged portion 36 having a cross-sectional area greater than the cross-sectional area of the wire and diameter of the coil to resist the coil from passing thereover. Alternatively, enlarged portion 36 may have a cross-section that allows the coil to be pulled over the enlarged portion. For example, the cross sectional diameter of the enlarged portion may be about equal to the inside diameter of the coil. The enlarged portion 36 also may be provided to cooperate with a release mechanism (see e.g., FIGS. 7A-F) as will be discussed in more detail below.

Enlarged portion 36 may be formed by attaching a member to the end of wire 34 by welding, gluing or other suitable attachment means or may be formed integrally with the wire by deforming the end of the wire. The other end of wire 34, also may include an enlarged portion 38 for engagement with a locking device or release mechanism, such as release mechanism 28 (see e.g., FIG. 3), as will be further described below. The enlarged portion 38 may be formed by deforming the end of wire 34 by swaging or arc welding, or attaching an enlarged portion to the end of the wire by welding, swaging, or other suitable means. Although enlarged portions 36 and 38 are shown with spherical and cylindrical configurations, other configurations or configuration combinations can be used. For example, both enlarged portions may be spherical or cylindrical, or portion 36 may be cylindrical and portion 38 spherical.

Figure 3:
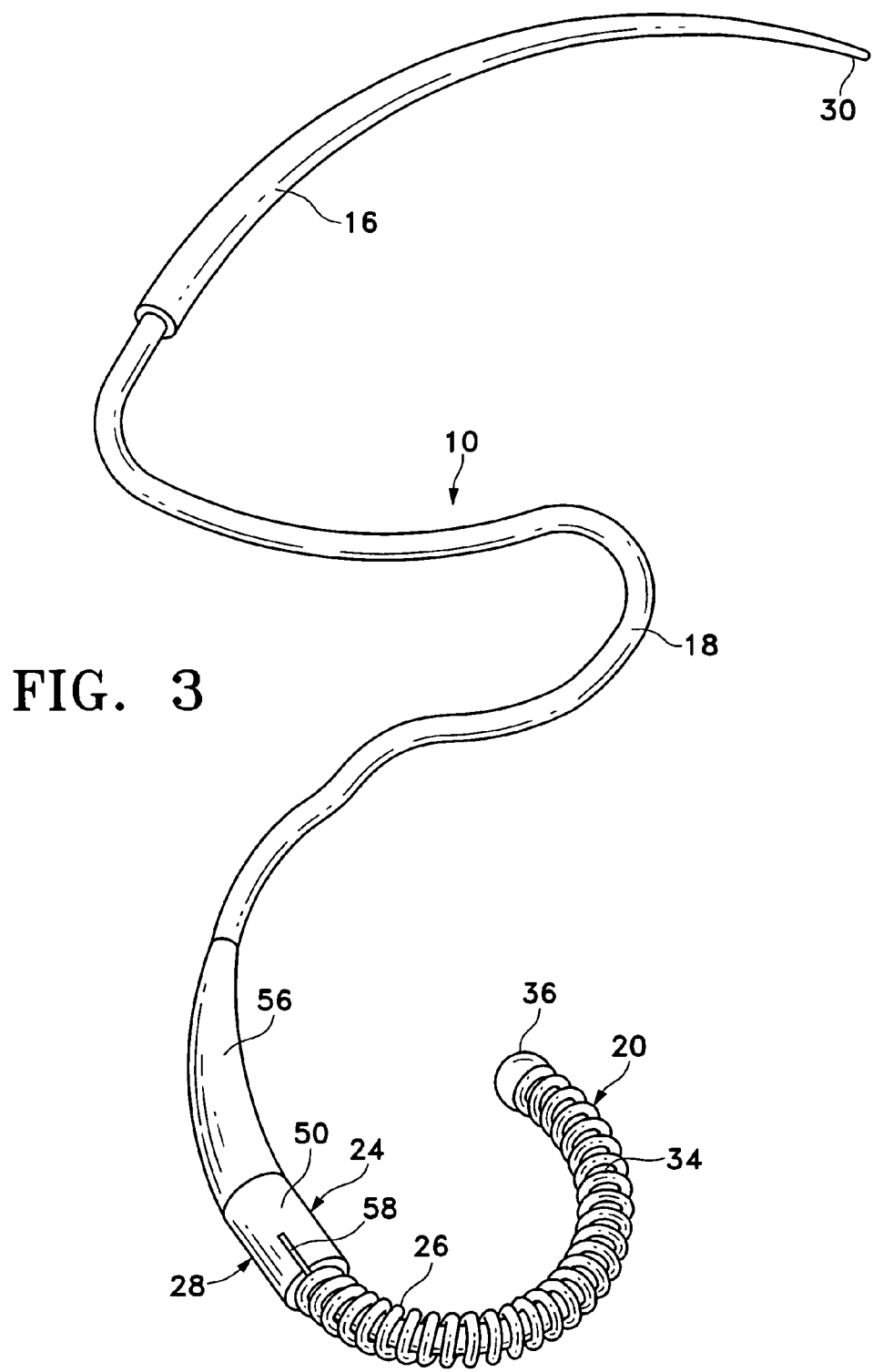
FIG. 3 is a tissue connector assembly, which may include the fastener of any of FIGS. 2A, 2B and C, or 2D and E.

Referring to FIGS. 2A and 3, fastener 20 is shown in open and closed configurations. When wire 34 is in an undeformed or closed configuration, the fastener is closed (FIG. 2A) for keeping or connecting tissue together. When wire 34 is in a deformed or open configuration, the fastener is open (FIG. 3) for insertion of the wire into tissue. As discussed above, wire 34 is in its closed configuration when in a relaxed state. Wire 34 is preferably not deformed past its yield point in its open position. Accordingly, it may have a U-shaped configuration in its open position to facilitate insertion of the wire through the tissue. However, other configurations may be used including, but not limited to C-shaped, V-shaped, J-shaped, and other similarly shaped configurations. Wire 34 is moved from its closed position to its open position by a restraining device which is further described below. When in its closed position, wire 34 forms a loop with the ends of the wire in a generally side-by-side or overlapping orientation.

Wire 34 may be formed by first wrapping the wire onto a mandrel and heat treating the wire at approximately 450-530 degrees Celsius for approximately 5 to 30 minutes. Wire 34 is then air quenched at room temperature. The mandrel may have a constant diameter or it may be conical in shape to facilitate forming the spiral configuration shown in FIG. 2A.

As shown in FIG. 2A, fastener 20 may have a generally conical shape along the longitudinal axis A, with a decreasing diameter as the radius of curvature of the fastener decreases. One or both ends of the fastener may extend in a substantially straight direction from the curved form of the wire 34. The straight sections or extensions may extend for a length equal to about two to three times the outside diameter of the coil 26 (as compared to the diameter of the loop) or about 0.010 to 0.020 inches. These extensions may allow the release mechanisms (discussed in detail below) to operate more efficiently and also may simplify manufacture of the fastener.

The fastener may be embodied by a wire (wire 34), having a cross-sectional thickness of about 0.0035 inches, which, in the closed configuration shown, forms an inner loop having a diameter $D_1$ of about 0.017 inches and an outer loop dimension $D_2$ (horizontally measured from inside of the loop) of about 0.021 inches. In the open configuration, the exemplary clip may form a U-shape with a depth of the U-shape being about 0.032 inch (0.8 mm).

Figure 2B:
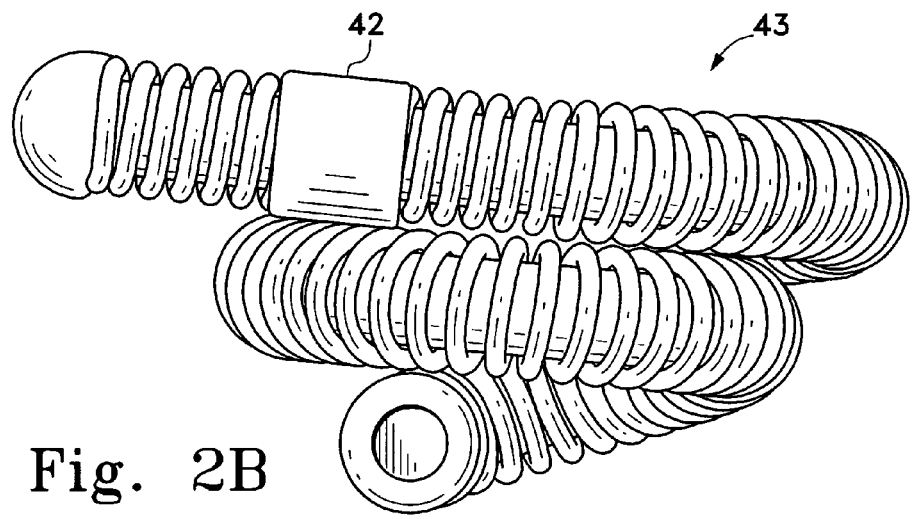
FIGS. 2B and 2C show a variation of the fastener of FIG. 2A.
Figure 2C:
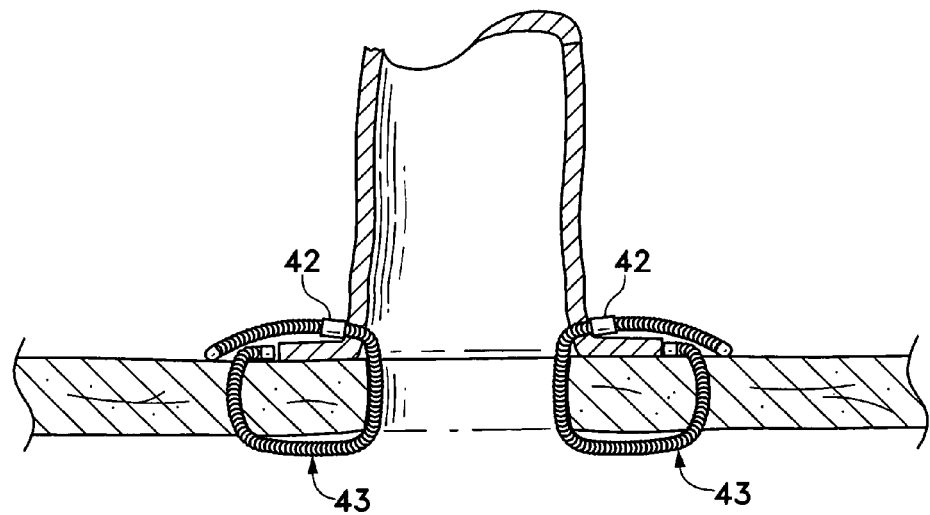

Referring to FIGS. 2B and 2C, a fastener 43 with two extensions and a stopper 42 is shown. The stopper preferably is slidably mounted onto the wire 34 in the vicinity of the transition from a curved wire portion, to the relatively straight extension. The stopper is placed between discrete springs and held in place thereby. This embodiment is particularly advantageous for anastamosing a relatively thin-=walled vessel to a relatively thick-walled vessel (e.g. the aorta or other large vessel), where an extension acts to prevent the relatively thin-walled vessel from sliding into the anastomosis site and out of the preferred position where it is to be fixed, as is illustrated in FIG. 2C.

This fastener design, for example, may be embodied by a wire (wire 34) having a cross-sectional thickness of about 0.045 inches, which, in the closed configuration shown forms an inner loop having a diameter $D_1$ of about 0.060 inches and an outer loop dimension $D_2$ of about 0.065 inches. In the open configuration, the fastener forms a U-shape with a depth of the U-shape being about 0.07-0.09 inch (1.5 to 2 mm).

It is to be understood that the fasteners may have undeformed or deformed configurations different than those shown or described herein. In addition, a locking clip (not shown) may also be attached to connect the ends of the fastener when the fastener is in its closed position to prevent possible opening of the fastener over time. The locking clip may also be integrally formed with one end of the fastener.

As shown in FIG. 2A, wire 34 is surrounded by spring or coil 26 which, along with the locking device 28, restrains the wire in its deformed configuration. Coil 26 comprises a helical wire forming a plurality of loops which define a longitudinal opening for receiving the shape memory alloy wire 34. Coil 26 may be formed from a platinum alloy wire having a cross-sectional diameter of approximately 0.0005-0.005 inch, for example. The helical wire may have other cross-sectional shapes and be formed of different materials. Coil 26 is preferably sized so that when in its free (uncompressed) state it extends the length of wire 34 with one end adjacent to enlarged portion 36 and the other end adjacent to enlarged portion 38. It is to be understood that the coil may not extend the full length of the wire. For example, a flange or similar device may be provided on an intermediate portion of wire 34 to limit movement of the coil along the length of the wire.

Coil 26 may be formed by wrapping a wire around a cylindrical mandrel thereby cold-working the wire into a coil shape having a straight axial configuration (not shown). Next, the coil 26 is axially slid over the wire 34 whereupon it takes on the substantially spiral shaped configuration of the wire 34. Next, a locking device such as 28, for example is locked in position over enlarged portion 38. Afterwards, an additional enlarged portion 36 is slid on the wire 34 and driven against the coil 26 to compress the same and open the fastener. When in the open position, the enlarged portion 36 is then fixed to the wire 34 by swedging or equivalent fixation technique. Next, any extension of the wire 34 beyond enlarged portion 36 is removed or cut off from the fastener assembly 20.

When fastener 20 is in its free state (with the wire in its undeformed configuration and the coil 26 having substantially no axial compression at its ends), loops of the coil are generally spaced from one another and do not exert any significant force on the wire 34 (FIG. 2A). When the coil 26 is compressed (with wire 34 in its deformed configuration), loops of the coil on the inner portion 46 of the coil are squeezed together with a tight pitch so that the loops are contiguous with one another while loops on the outer portion 48 of the coil are spaced from one another. This is due to the compressed inner arc length of coil 26 and the expanded outer arc length of the coil. The compression of the loops on the inner portion 46 of coil 26 exerts a force on the inner side of wire 34 which forces the wire to spread open (i.e., tends to straighten the wire from its closed configuration to its open configuration). The end of coil 26 adjacent enlarged portion 36 is held in a fixed position relative to wire 34. The opposite end of coil 26 is free to move along wire 34 and is held in place when the coil is in its compressed position by locking device 28. It should be understood, however, that a coil (not shown) having sufficient stiffness, for example, may be used where adjacent loops do not contact one another when the coil is compressed to force wire 34 into an open position.

Figure 2D:
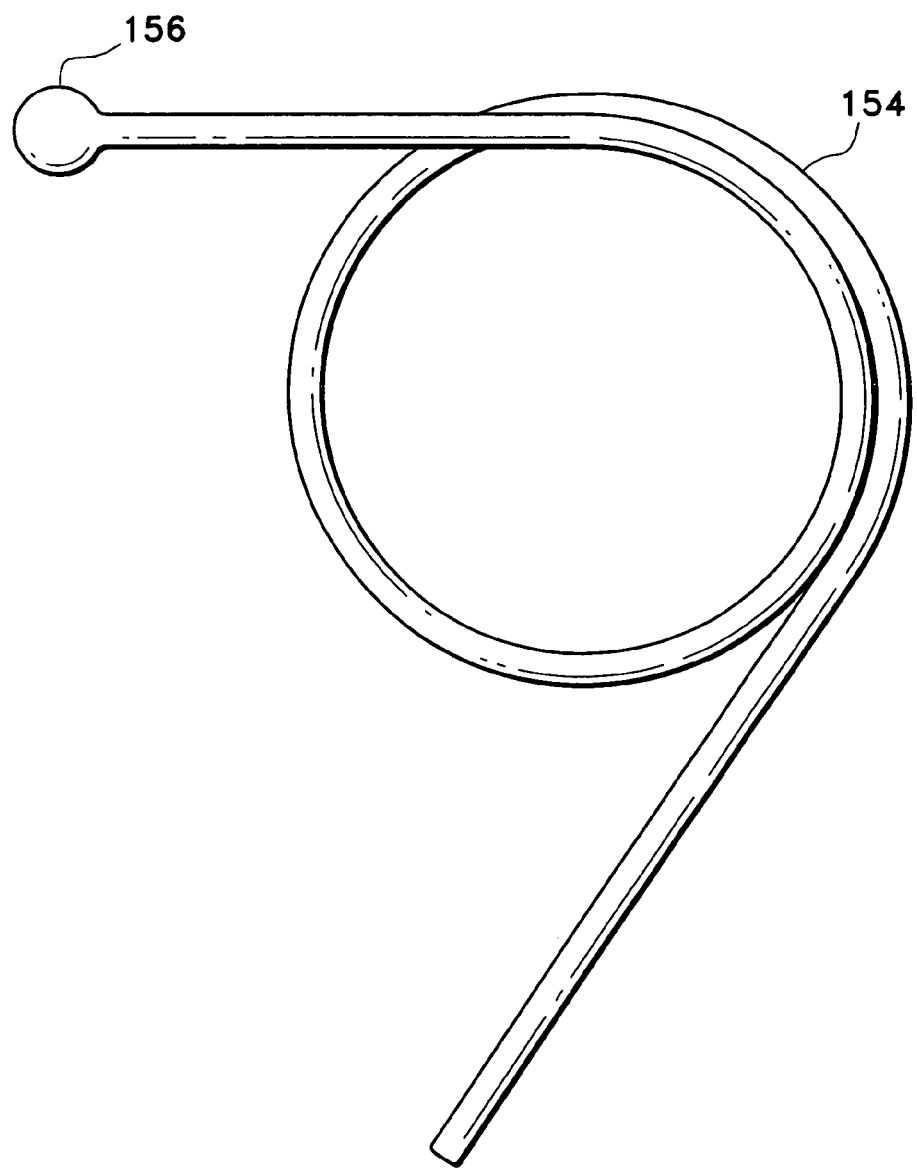
FIGS. 2D and 2E illustrate portions of another fastener embodiment that may be used with the apparatus of FIG. 1.
Figure 2E:
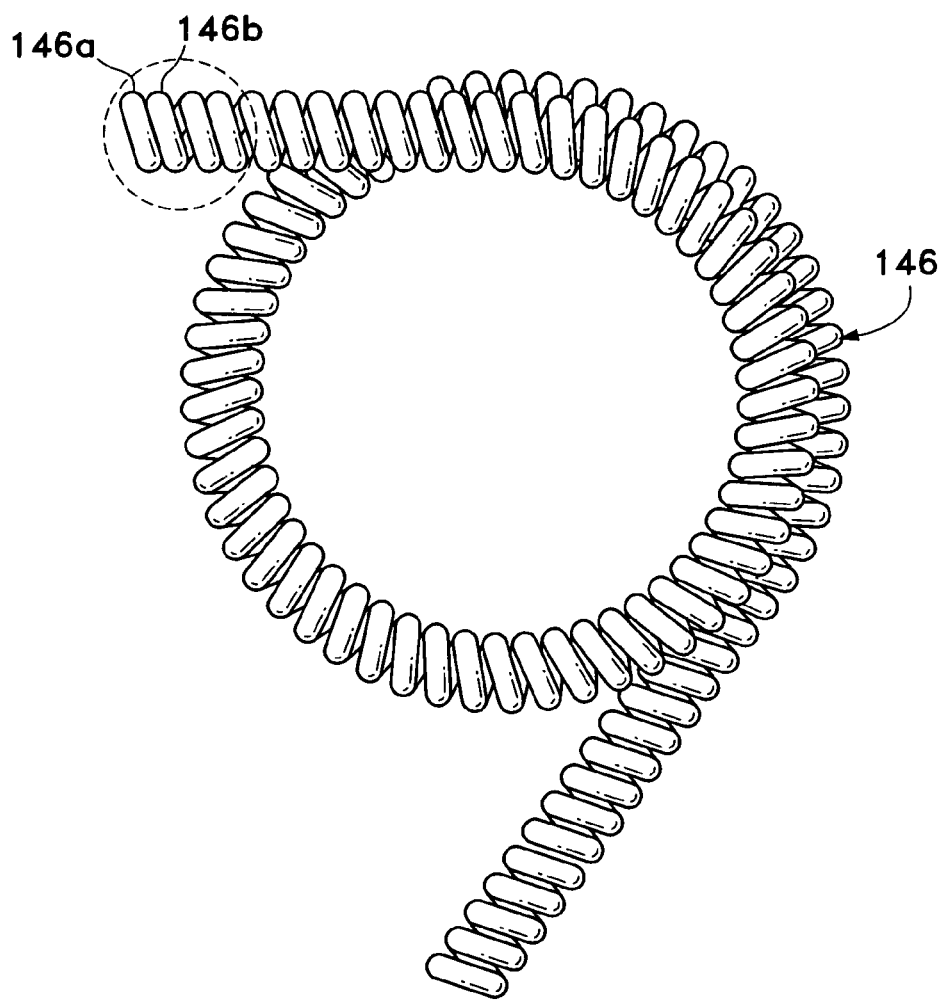

Referring to FIGS. 2D-2E, another fastener construction will be described where a fastener is formed such that the coil 146 assists the wire 154 in its return to the closed state. In this embodiment, the coil 146 forms an integral part of the fastener (i.e., fastening system) so as to assist in the closing thereof. A double memory feature of this construction provides both the coil 146 and wire 154 with a memory biased to the closed position or state of the fastener. In making the fastener, the wire 154 may be first formed in a generally spiral shaped configuration shown in FIG. 2D. The wire 154 is wound on a clip fixture, e.g., a tapered shaft (not shown) and is then heat treated in a first heat cycle, in a convection oven set at a temperature ranging from about 450° C. to less than about 500° C. for a period of about one to twenty minutes to set the desired shape (e.g., the shape shown in FIG. 2D) of the bare clip 154. In one example, the wire is heated in a first heat cycle at a temperature of about 475° C. for about six minutes. The first heat cycle does not fully remove the cold worked aspect of the wire 154, since the first heat cycle is performed below 500° C. Of course, the wire 154 may be formed in various other configurations, some examples of which are described in application Ser. No. 09/090,305, the entire contents of which are hereby incorporated by reference thereto. Enlarged portion 156 is formed prior to the first heat cycle of the wire 154, and may be formed by attaching a member to the end of wire 154 by welding, gluing or other suitable attachment means or may be formed integrally with the wire by deforming the end of the wire, such as by heat (melting).

Coil 146 is formed by first wrapping a wire of shape memory material, such as NITINOL around a cylindrical mandrel (not shown) and then heat setting the wire in a first heat cycle of the coil, by placing it and the mandrel in a convection oven set at a temperature ranging from about 450° C. to less than about 500° C. for a period of about one to twenty minutes to set it in an axially straight, configuration (not shown). In one example, the coil is heated in a first heat cycle at a temperature of about 475° C. for about six minutes. For an even stiffer configuration with correspondingly greater spring recoil, a pair of Nitinol wires (each having about the same length and diameter as coil 146) 146a,146b may be wound around the cylindrical mandrel and then the pair may be heat set in a first heat cycle by placing it and the mandrel in a convection oven and heat treating according to the parameters described above, to set it in an axially straight, double coil configuration (not shown). Of course, other materials which exhibit a sufficient shape memory ability could be substituted for Nitinol, as would be apparent to one of ordinary skill in the art. Also, more than two adjacent wires (e.g., 3, 4 or more) may be wrapped and heat set in a similar procedure.

Next, the coil 146 (whether a single coil or a double coil, or more, is used) is axially slid over the wire clip 154, such that the leading end of the coil 146 abuts or lies adjacent to the enlarged portion 156, whereupon it takes on the substantially spiral-shaped configuration of the wire 154. Once in position on the wire 154, the assembly (wire 154 and coil 146) is again heat treated, in a second cycle, this time in a salt bath, to form an integrated system, wherein the shapes of both components are formed to one another so as to function in concert upon closing of the fastener. The salt bath may be sodium nitrate and potassium nitrate in a 50/50 mixture by weight percent, for example. Alternatively, other molten mixtures could be used as would be apparent to those of ordinary skill in the art. The purpose of the salt bath is to provide a much more stable process, with more efficient and constant heat transfer to the entire assembly, thereby optimizing the strength of the fastener by removing any residual cold-worked stress in the materials to optimize the configuration of the fastener.

The salt bath is heated to a temperature of about 500-530° C. and the fastener is submerged therein for a period of about one to six minutes. In one example, the fastener may be submerged in a salt bath having a temperature of about 515° C. for about two minutes. The shape of the coil 146 after treatment in the salt bath cycle, is memory set into the shape of the clip 154, as shown in FIG. 2E, for example, so that each component has a substantially spiral-shaped memory set. Of course, other shapes of the wire 154 could be made initially, as noted above, after which the coil 146 would be processed in the same way as described above, to take on a memory set provided by the shape of the wire 154.

After heat setting as described above, the fastener is assembled with a locking mechanism, much in the same manner as described above with regard to previous embodiments. Although the enlarged portions have been described with spherical and cylindrical configurations, other configurations or configuration combinations can be used. For example, both enlarged portions may be spherical or both may be cylindrical, etc.

When the double memory fastener is in its free state (i.e., with the wire 154 in its undeformed configuration and the coil 146 having substantially no axial compression forces applied to its ends), loops of the coil are generally spaced from one another and do not exert a substantial force on the wire 154. This is because of the memory set that was fixed in the coil 146 during the preparation of the double memory fastener as described above. Because the memory of the coil 146 has been formed to take on essentially the same configuration as the memory set of the wire 154 when no external forces are applied to the fastener, the coil 146 does not "fight against" the closure of the wire 154 as it moves toward its free state. FIG. 2E shows that even if the coil 146 is removed from the clip 154, it will still assume the general spiral-shaped configuration (or other configuration to which its memory was set while mounted on a wire 154). Thus, the free state of the coil 146 cooperates with the free state of the wire 154.

A more thorough description (including additional drawings) of double memory fasteners can be had by referring to the copending and commonly assigned application filed concurrently herewith, titled "Multiple Bias Surgical Fastener," which application was assigned application Ser. No. 09/541, 397. The same application is hereby incorporated by reference thereto, in its entirety. The same application is hereby incorporated by reference thereto, in its entirety.

In addition, fasteners may be formed in still other configurations. One or both ends of the fastener may extend in a substantially straight direction from the curved form of the wire 154. The straight sections of extensions may extend for a length equal to about two to three times the outside diameter of the coil 146 (as compared to the diameter of the loop) or about 0.010 to 0.020 inches. These extensions may allow the release mechanisms (discussed in detail below) to operate more efficiently and also may simplify manufacture of the fastener.

The fastener may be embodied by a wire (a small clip), having a cross-sectional thickness of about 0.0035 inches, which, similar to the closed configuration of the fastener shown in FIG. 2A, forms an inner loop having a diameter $D_1$ of about 0.017 inches and an outer loop dimension $D_2$ (horizontally measured from inside of the loop) of about 0.021 inches. In the open configuration, the exemplary clip may form a U-shape with a depth of the U-shape being about 0.032 inch (0.8 mm).

In the embodiment shown in FIG. 3, the tissue connector assembly 10 generally comprises a tissue piercing or penetrating member 16, a flexible member 18, and a fastener or surgical clip 20. A restraining device, generally indicated at 24 and comprising a spring (or coil) 26 and a locking device (or coupling member) generally indicated at 28, is connected to the fastener 20 for holding the fastener in a deformed configuration as further described below. Of course, alternative embodiments of the surgical clip, e.g., employing a wire 154 and a coil 146, or multiple coils as described above, could be used alternatively in the arrangement.

Piercing or penetrating member 16, which may be in the form of a needle (such as a 7-0 or 8-0 needle), has a sharp pointed tip 30 at its distal end for penetrating tissue. Piercing member 16 may be bent as shown in FIG. 3, for example. The diameter of at least a portion of piercing member 16 is preferably greater than the diameter of flexible member 18 so that the flexible member can easily be pulled through an opening formed in the tissue by the needle. The distal end of piercing member 16 is preferably rigid to facilitate penetration of tissue. The remaining length of piercing member 16 may be rigid or flexible to facilitate movement of the needle through the tissue as further described below. The tip 30 of piercing member 16 may have various configurations and may, for example, be conical, tapered, or ground to attain a three or four facet tip. Piercing member 16 may be made from stainless steel or any other suitable material. It is to be understood that piercing member 16 may have a shape or radius of curvature other than the one shown. Piercing member 16 may also be integrally formed with the flexible member 18 (e.g., both needle and flexible member formed of the same material.)

Flexible member 18 may be in the form of a suture formed from conventional filament material, metal alloy such as Nitinol, polymeric material, or any other suitable material. The material may be non-stretchable or stretchable, solid or hollow, and have various cross-sectional diameters. The flexible member or suture may have a cross-sectional diameter of 0.003 inch, for example. The diameter and length of the suture will vary depending on the specific application. The suture may be attached to piercing member 16 by crimping or swaging the piercing member onto the suture, gluing the suture to the piercing member, or any other suitable attachment method. Flexible member 18 may have cross-sectional shapes other than the one shown herein and may have other constructions as well.

Referring to FIGS. 4A and 4B, one release mechanism for coupling the fastener to the suture and needle is generally indicated with reference numeral 28a. Locking device or release mechanism 28a comprises a plurality of substantially rigid strands, preferably wires 106, arranged substantially parallel to one another and circularly about a longitudinal axis of the aligned strands to form a tube-like configuration as can be seen in the cross-sectional view of FIG. 4B. Alternatively, strands 106 may be cables or some other substantially rigid strand elements arranged in the same manner as the wires shown in FIG. 4B. Upon arrangement into the circular configuration, the hidden or blind end portions 106a of the strands are coupled to tapered section 2, which is coupled to a piercing member or needle through a flexible member such as flexible member 18.

A rod 162 may extend from tapered section 2 to facilitate fixation or coupling of the strands thereto. The coupling of the strands to tapered section 2 is preferably accomplished by gluing or soldering to rod 162, although other equivalent or similar known joining techniques may be employed (e.g. welding, threadably attaching, etc). Similarly, rod 162 is preferably glued, soldered or threaded into the needle or transition element. In an alternate arrangement, the flexible member may extend through tapered section 2 and form a substitute structure for rod 162. This may be preferred when the flexible member is a metal wire.

The end portions 106b of the strands in the vicinity of the fastener include notches 109 which are formed into the strands to a depth equal to approximately half the diameter of the strand 106. When the strands are arranged in the circular configuration described above, the notches 109 form a chamber 108 configured for receiving and holding enlarged portion 38. Although enlarged portion 38 is shown as having a spherical shape, it may have other shapes as discussed above including a barrel or cylindrical shape, or other shape that may be easily grasped and easily released. The notches are preferably placed about 0.015" from the free ends of the strands, but this distance, of course, can be modified, depending upon, for example, the amount of compression of spring 26 that is desired when ball 38 is inserted into and held by notches 109.

After placement of ball 38 within chamber 108 formed by notches 109, a shrink wrap layer, preferably a shrink tubing 110 may be provided over at least free end portions 106b of wires or strands 106, and the tubing heated to compress against strands 106 and hold them in place against ball 38, preferably symmetrically against ball 38. Together, tubing 110 and strands 106 effectively hold ball 38 captive within notches 109. Alternatively, other plastic or elastic restraining members may be mounted around the free end portions of the wires or strands to aid in maintaining them in place, preferably symmetrically against ball 38. Still further, strand members may be designed with an elastic spring force sufficient to maintain notches 109 in place with sufficient force to maintain the ball 38 captive therein under the tensile forces normally experienced during a suturing procedure. Although a seven strand embodiment is shown, it should be understood that fewer or more than seven strands may be used. The number of strands may vary depending on, for example, the size of the clip or the size of the strands. Typically, the number of strands may range from two to ten. In a coronary anastomosis, the number of strands preferably will range from five to seven although other numbers may be used.

In assembly, enlarged portion 38 of wire 34 is placed in chamber 108. Tubing 110 is wrapped around at least a portion of the strands (as shown in the drawings) and heated to maintain enlarged portion 38 captive within the cavity formed by the strands. Compression coil or spring 26 (or alternatively, coil 146 or multiple coil 146a,146b, etc.) is slid over wire 34 (or alternatively, wire 154) and compressed against end portions 106b such that the fastener is in its open configuration. Enlarged portion 36 may then be formed at the other end of or attached to wire 34 to maintain the fastener in its open configuration. As noted above, when a coil 146 or multiple coil 146a,146b (or coil having more than two wires forming it) is employed, the coil remains integral with the wire 154 upon closing of the fastener 140. The closing actions or forces provided by the wire 154 and coil 146 act in concert to provide an optimal closing force of the fastener upon the tissues, tissue and graft, etc. The coil 146 remains integral with the wire or clip 154 after closing of the fastener 140, and both components cooperate to maintain the anastomosis.

Release mechanism 28a is movable between a locked position and an unlocked position. In the locked position the ball 38 is held within notches 109 and consequently, coil 26 is held in its compressed position, thereby maintaining fastener wire 34 in its deformed or open position. In the unlocked position, ball 38 is released from the notches, thereby allowing the coil 26 to expand, which causes the fastener wire 34 to close.

Movement of the release mechanism to the open position is accomplished by applying a compressive force to the bundle of strands 106 between the enlarged portion 38 and blind ends 106a. The compressive force may be applied at any opposing locations around the circumference of the shrink tube. The implement applying the force preferably is oriented at an angle to the strands, preferably substantially perpendicular thereto, to deform the portions between ball 38 and blind ends 106b radially inward. As those portions are compressed, shrink tube 110 and strands 106 change from a circular configuration to a somewhat elliptical configuration. Some of the notches 109 move away from ball 38, facilitating its removal from the locking device 28a.

Figure 5A:
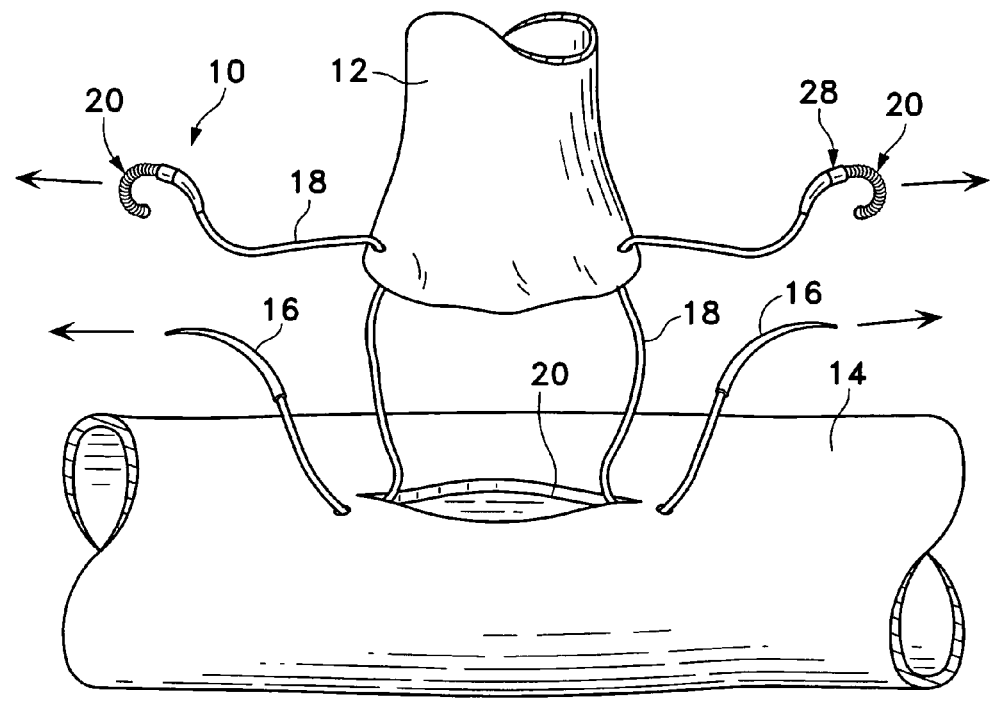
FIGS. 5A, 5B and 5C diagrammatically illustrate placement of a fastener in an anastomosis.
Figure 5B:
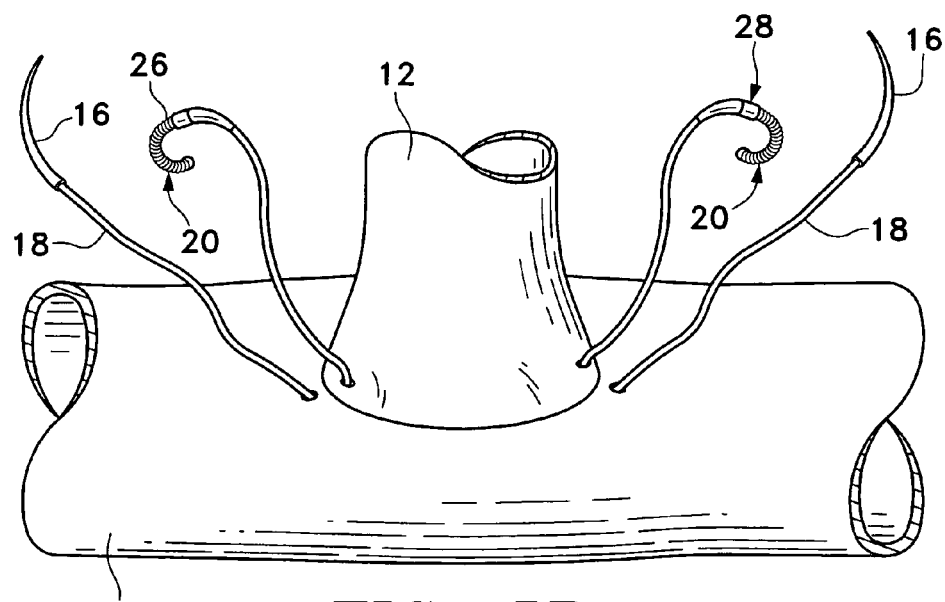
Figure 5C:
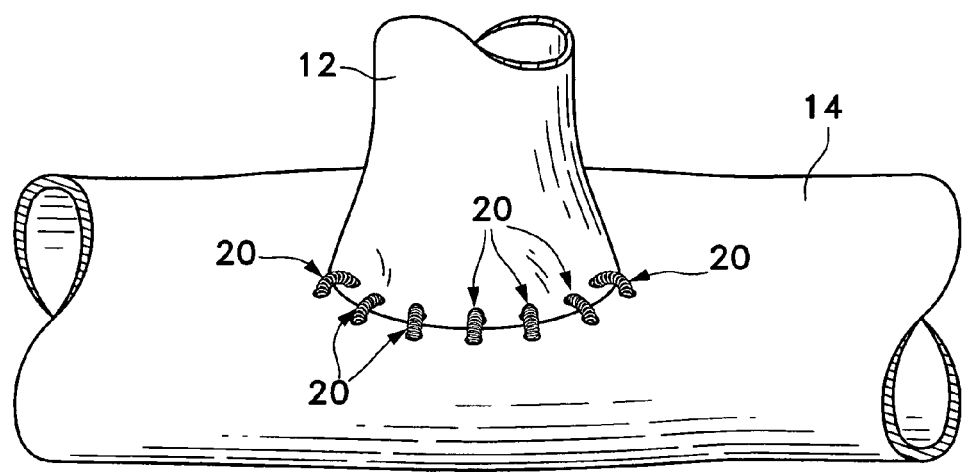

The tissue connector assembly 10, has many uses. It may be especially useful for minimally invasive surgical procedures including creating an anastomosis between a vascular graft 12 and an artery 14 (FIGS. 5A-5C). The anastomosis may be used to replace or bypass a diseased, occluded or injured artery. A coronary bypass graft procedure requires that a source of arterial blood flow be prepared for subsequent bypass connection to a diseased artery. An arterial graft may be used to provide a source of blood flow, or a free graft may be used and connected at the proximal end to a source of blood flow. Preferably, the source of blood flow is one of any number of existing arteries which may be dissected in preparation for the bypass graft procedure. In many instances it is preferred to use the left internal mammary artery (LIMA) or the right internal mammary artery (RIMA), for example. Other vessels which may be used include the saphenous vein, gastroepiploic artery in the abdomen, radial artery, and other arteries harvested from the patient's body as well as synthetic graft materials, such as DACRON® (polyester fibers) or GORETEX® (expanded polytetrafluoroethylene). If a free graft vessel is used, the upstream end of the dissected vessel, which is the arterial blood source, will be secured to the aorta to provide the desired bypass blood flow, as is well known by those skilled in the art. The downstream end of the graft vessel is trimmed for attachment to an artery, such as the left anterior descending coronary (LAD). It is to be understood that the anastomosis may be formed in other vessels or tissue. Use of tissue connector assembly 10 in a coronary bypass procedure will now be discussed.

The patient is first prepped for standard cardiac surgery. After exposure and control of the artery 14, occlusion and reperfusion may be performed as required. An arteriotomy is performed on artery 14 to provide an opening 120 for receiving a graft vessel (FIGS. 5A-5C). After the snared graft vessel 12 has been prepared and made to the appropriate length as would be conventional in the art, a tissue connector assembly 10 is attached to the free end of the graft vessel along an edge margin of the vessel. In order to attach the connector assembly 10, the surgeon grasps the needle 16 with a needle holder (e.g., surgical pliers, forceps, or any other suitable instrument) and inserts the needle 16 into the tissue of the graft vessel 12 in a direction from the exterior of the vessel to the interior of the vessel. The surgeon then releases the needle 16 and grasps a forward end of the needle which is now located inside the graft vessel 12 and pulls the needle and a portion of the suture 18 through the vessel. The needle 16 is passed through an opening 120 formed in the sidewall of the artery 14 and inserted into the tissue of the artery in a direction from the interior of the artery to the exterior of the artery. The surgeon then grasps the needle 16 located outside the artery 14 and pulls the needle and a portion of the suture 18 through the arterial wall. A second tissue connector assembly 10 may be inserted similarly at a location generally 180 degrees from the location of the first tissue connector in a conventional "heel and toe" arrangement.

Once the tissue connector assemblies 10 are inserted, the graft vessel 12 is positioned above and aligned with the opening 120 in the sidewall of the artery 14 (FIG. 5A). A section of each suture 18 is located between the graft vessel 12 and artery 14. The fasteners 20 and needles 16 are pulled generally away from the artery 14 to reduce the length of the suture 18 (eliminate slack of the suture) between the vessel 12 and artery and "parachute" the vessel onto the artery (FIG. 5B). The needles 16 are then pulled away from the artery 14 until each fastener 20 is positioned within the graft vessel 12 and artery with one end of each fastener 20 extending from the vessel and the opposite end of each fastener extending from the artery.

A surgical instrument (e.g., needle holder) is used to radially squeeze each locking device 28, such as locking device 28a, to release the locking device from the fastener 20. Upon removal of the locking device 28, the coil 26 moves to its free uncompressed state which allows the wire 34 to return to its original undeformed closed position (FIG. 5C). As the wires 34 move to their closed position the adjacent tissues of the graft vessel 12 and artery 14, which were previously pulled together and placed in the open fastener are squeezed to securely hold the graft vessel and artery together. The graft and arteriotomy edges may be abutted or everted as is known in the art. It should be noted that as the locking device 28 is squeezed, two steps are accomplished. The fastener 20 is released from the locking device 28, thus allowing coil 26 to expand and wire 34 to move to its closed configuration. The needle 16 also is released from the fastener. Thus, in this embodiment, the locking device 28 provides for simultaneous fastener closure actuation and needle release.

In this example, two tissue connector assemblies 10 are used to make connections at generally opposite sides of the graft vessel. Additional tissue connector assemblies 10 may be used to make connections between those. The procedure may be accomplished with a beating heart procedure with the use of a heart stabilizer to keep the heart stable during the procedure. The procedure may also be performed endoscopically.

As an alternative to inserting tissue connector assemblies 10 at "heel and toe" locations described above, a number of tissue connectors 10 may be inserted generally around the location of the heel. The graft vessel may then be pulled towards the artery to determine whether the opening formed in the sidewall of the artery is large enough before completing the anastomosis. In a further alternative, double needle assemblies (FIG. 6 described below) and single needle assemblies are used. Each needle of a double needle assembly 11 is passed from inside to outside of the respective graft and artery. The first assembly is placed at the "heel" (6 O'clock) position, the tissue brought together in the clip and the clip closed. Another double needle assembly is then placed a the 5 O'clock position and closed, 7 O'clock position and closed, 12 O'clock position and closed, 1 O'clock position and closed, 11 O'clock position and closed. Three single needle assemblies 10 are then evenly spaced between the 6 and 12 O'clock positions (placed laterally) and the tissue placed therein. These clips are then closed. Three more single needle assemblies 10 are placed on the other lateral side of the anastomosis in the same manner as the first lateral fasteners.

Figure 6:
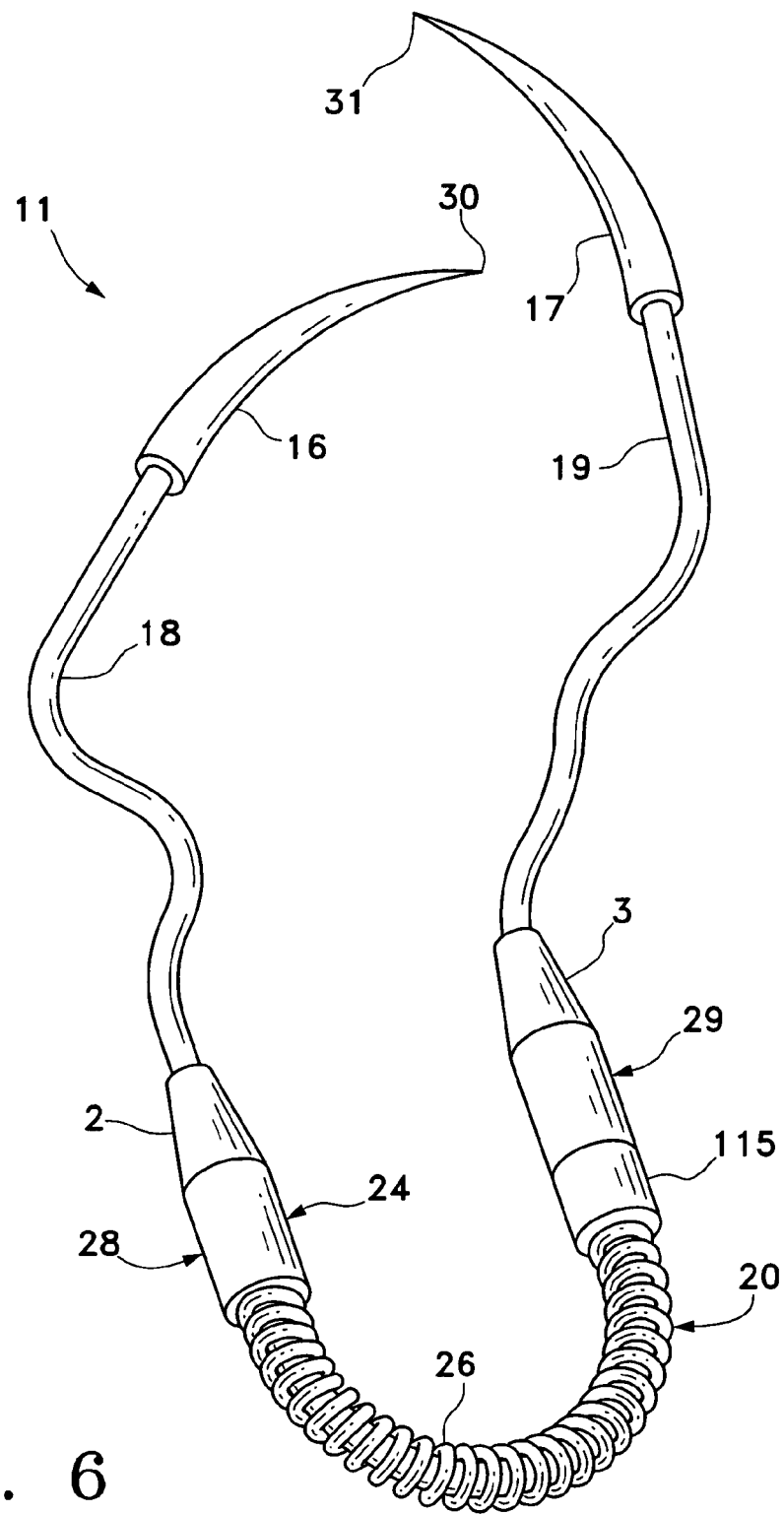
FIG. 6 shows a double needle tissue connector assembly.

Referring to FIG. 6, a tissue connector assembly 11 having multiple piercing members is shown. A multiple piercing member construction facilitates threading ends of the assembly from inner to outer wall(s) of material, such as tissue, which may eliminate or minimize the possibly of dislodging material, such as plaque, from the inner wall of calcified arteries, for example, as will become more apparent from the description provided below. In a preferred embodiment, two piercing members, each of which may comprise a needle, are releasably coupled to a fastener. The coupling between the flexible member (and, thus, the piercing member) and the fastener may be constructed to actuate closure of the fastener upon release of the flexible member (or piercing member). For example, the coupling may hold a compression spring (which is positioned around a fastener) in a compressed state to brace the fastener open and releasably lock or secure the fastener to the flexible member (or piercing member).

As shown in FIG. 6, a tissue connector assembly 11, which generally comprises tissue piercing or penetrating members 16 and 17, flexible members 18 and 19, and a fastener 20 (e.g., a surgical clip) is shown. A restraining device, generally indicated at 24 and comprising a spring (or coil) 26 and a locking device (or coupling member) generally indicated at 28 and 29, are connected to fastener 20 for holding the fastener in a deformed or open configuration as will be further described below. Penetrating or piercing member 17 may be made in accordance with the description provided above in connection with penetrating member 16, and, thus may, for example, be in the form of a needle (such as a 7-0 or 8-0 needle) having a sharp pointed tip 31 at its distal end for penetrating tissue. Members 16 and 17 may be the same or differ from one another. Flexible members 18 and 19 and tapered portions 2 and 3 also may have the same construction, which is preferred.

Referring to FIG. 7A, a release mechanism 28a also may be used as release mechanism 29 to releasably couple the other end of the fastener to another flexible member such as flexible member 19, which in turn, is coupled to a needle such as needle 17 as shown in FIG. 6. In this arrangement, a member or stopper 115, which may be annular, is secured to the other end of the fastener or wire 34 to prevent enlarged portion 36 from passing through the compression spring upon release from release mechanism 28a.

FIGS. 7B and 7C illustrate a synchronized fastener release system. One release mechanism may correspond to mechanism 28a. At the other end of the fastener or wire 34, a release mechanism which responds to the compressive state of coil 26 and releases the fastener or wire 34 upon release of compressive forces on the coil is shown and generally designated with reference numeral 29a. Referring to FIGS. 7B and 7C, release mechanism 29a comprises two members 121, each having a recess 122 formed therein and arranged to form chamber 124 when members 121 are aligned as shown in FIG. 7B. Recesses 122 are configured to retain enlarged portion 36, which is shown with a cylindrical configuration, but may have a spherical or other suitable shape for operatively associating with a suitably configured chamber. Further, members 121 may have semicircular transverse cross sections or some other combination of transverse shapes that can collectively provide the desired chamber to retain enlarged portion 36. The number of members 121 also may vary as would be apparent to one of ordinary skill.

Release mechanism members 121 have tapered ends 126, which are configured for positioning between coil 26 and fastener wire 34 as shown in FIG. 7B. When tapered ends 126 are so positioned and coil 26 is in a compressed state, coil 26 holds tapered ends 126, which are normally biased away from each other, sufficiently together to retain enlarged portion 36 within chamber 124. When release mechanism 28a (FIG. 4A) is actuated (e.g., radially compressed) to release enlarged portion 38 of fastener wire 34, coil 26 assumes its relaxed state, thereby releasing tapered ends 126 of release mechanism 29a from the coil and allowing the tapered ends to radially expand and release enlarged portion 36 of fastener wire 34. Accordingly, both needles and flexible members may be decoupled from the fastener when release mechanism 28a is actuated.

Figure 7D:
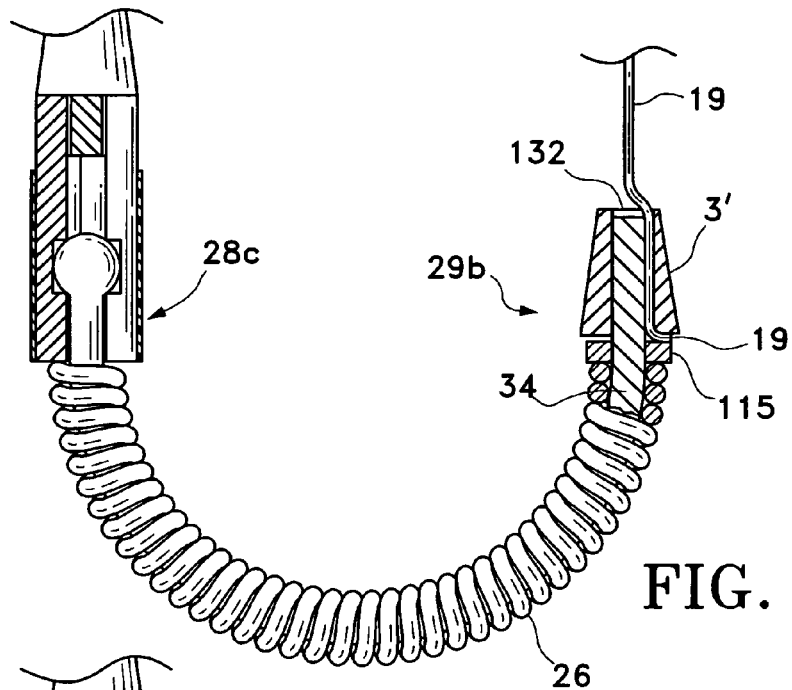
FIGS. 7D, E and F show another release mechanism that may be used with the second needle in the assembly of FIG. 6, where
Figure 7E:
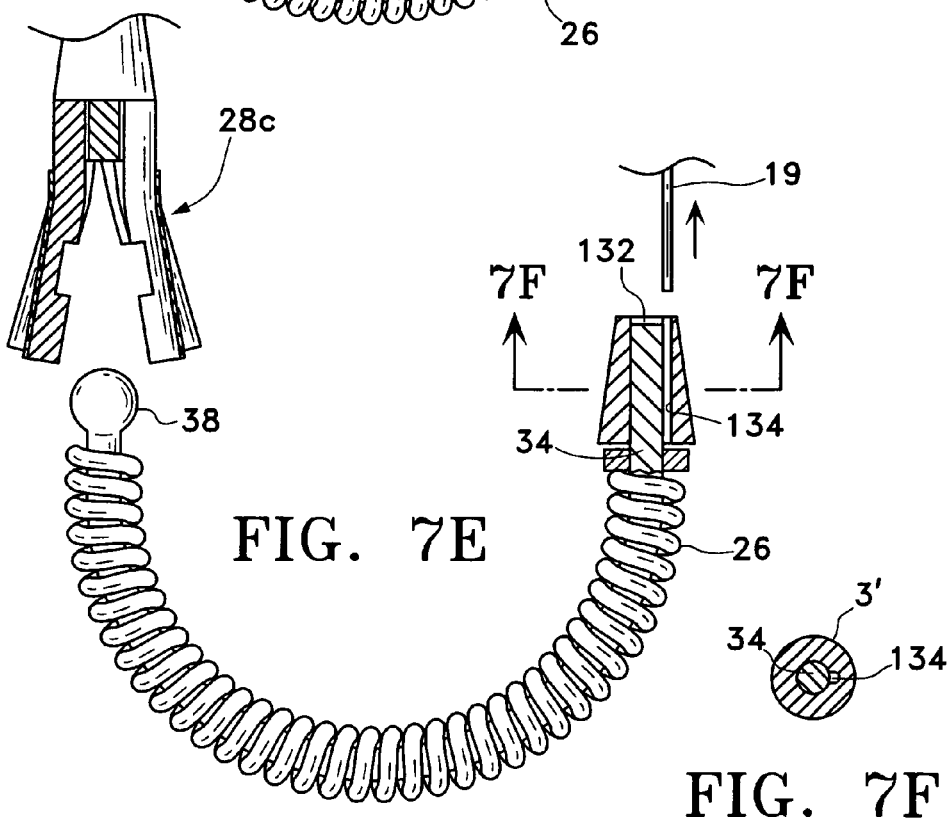
Figure 7F:
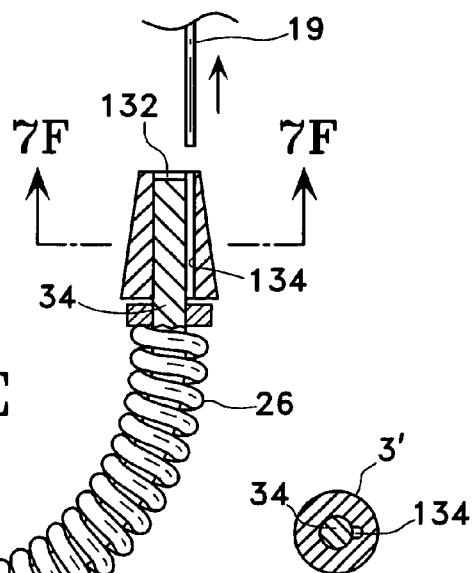
FIG. 7F is a transverse cross-sectional view taken along line 7F-7F in FIG. 7E.

FIGS. 7D-7F show another synchronized fastener system which is the same as the system described with reference to FIGS. 7A-7C with the exception of release mechanism 29b and the cooperating portion of the fastener or wire 34 being substituted for release mechanism 29a. In this embodiment, a member or stopper 115, which may be annular, is slidably coupled to fastener wire 34. Member 115 is configured to resist passage of coil 26 thereover. Accordingly, member 115 may have an outer diameter slightly greater than at least the portion of the coil adjacent thereto. A tapered or frustoconical member 3' is secured to an end of fastener wire 34, which need not include an enlarged portion. Member 3' is the same as member 3 with the exception that member 3' has a channel 134 for receiving flexible member or suture 19. Channel 134 extends radially outward from bore 132, which is formed through member 3', for receiving the fastener or wire 34.

Flexible member 19 is threaded through channel 134 and between tapered member 3' and annular member 115. When coil 26 is in a compressed state as shown in FIG. 7D, the coil urges member 115 toward tapered member 3' and compresses flexible member 19 therebetween. In this manner, flexible member 19 is secured to the fastener or wire 34. When release mechanism 28c is actuated (e.g., radially compressed) to release enlarged portion 38 of the fastener or wire 34, coil 26 assumes its relaxed state so that annular member 115 may slide away from tapered member 3' and release flexible member 19. Accordingly, both needles and flexible members may be removed from the fastener when release mechanism 28c is actuated. Although a metal flexible member may be used, a polymeric flexible member may be preferred.

Because of its potentially very small size and its tendency to wrap itself snugly around tissue, the fastener may not leave much to grab onto for its removal if desired. In addition, there may be no free ends to grab, which may make it difficult to remove without damaging the tissue around which it is wrapped. The following is a detailed description of apparatus and methods for removing undesirably placed fasteners in accordance with the present invention.

Figure 8A:
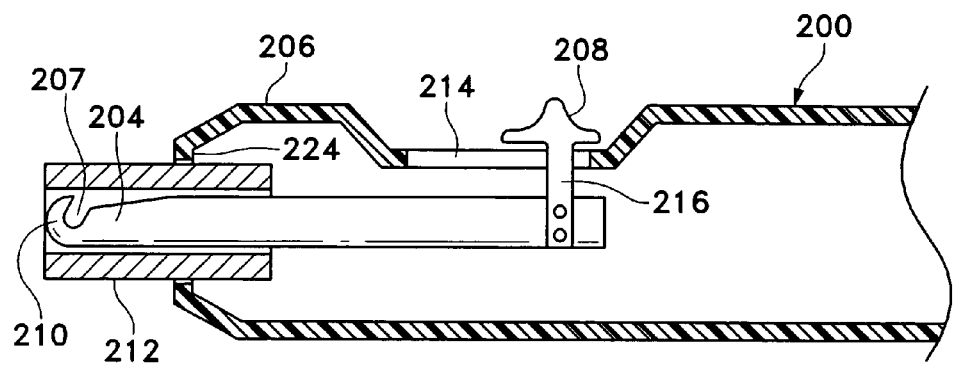
FIGS. 8A, 8B and 8C show fastener removal apparatus in accordance with the present invention where
Figure 8B:
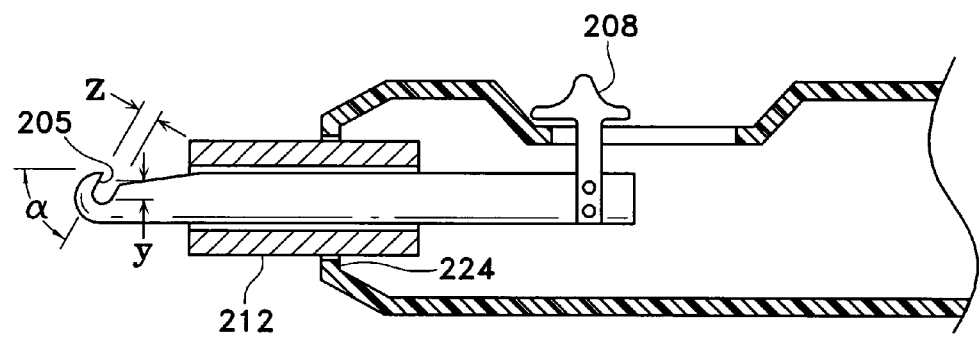
Figure 8C:
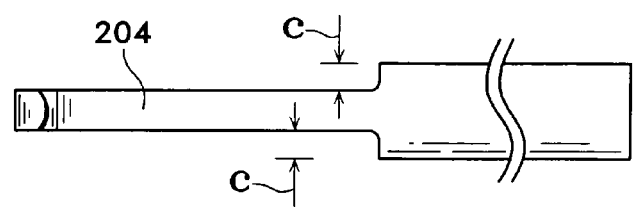
Figure 9A:
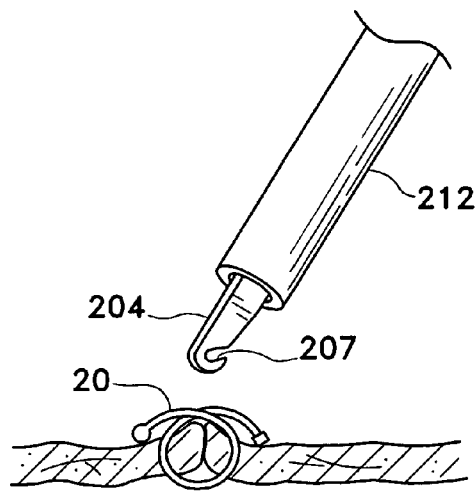
FIGS. 9A, 9B, 9C and 9D diagrammatically illustrate removal of a fastener with the apparatus of FIGS. 8A-C.
Figure 9B:
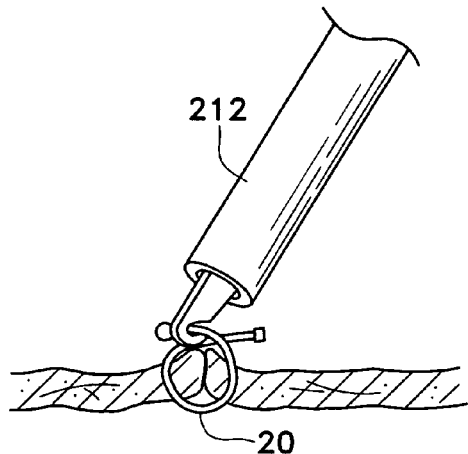
Figure 9C:
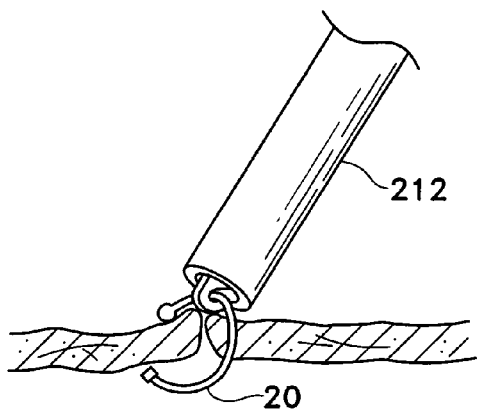
Figure 9D:
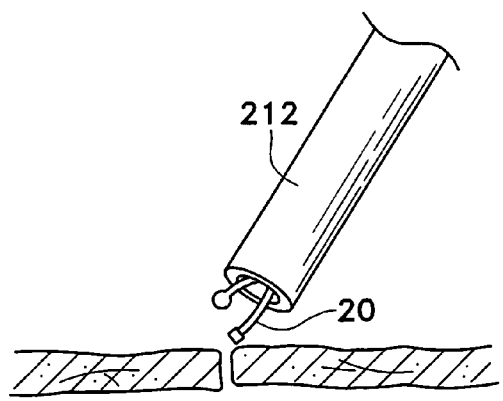

Referring to FIGS. 8A-8C, one embodiment of a removal apparatus of the present invention is shown in accordance with the present invention. In this embodiment, removal apparatus 200 generally comprises a grabber member 204 having a hook 210 and slidably mounted within tubular member or sleeve 212. Sleeve 212 may have a blunt distal end so that it may restrain tissue movement as the fastener is drawn therefrom. Sleeve 212 may be mounted within housing 206, which includes a slot 214 through which flange 216 of sliding button or actuator 208 is disposed. One end of the flange 216 is secured to the grabber member so that the grabber member can be withdrawn and extended from the sleeve as shown in FIGS. 8A and 8B respectively.

The hook slot or groove 207 may be formed at an angle of about 50-70 degrees ($\alpha$) (the angle is measured between the distal surface 205 of slot 207 and the longitudinal axis or surface of the upper grabber member 204) and has a width ("z") and depth ("y") slightly larger than the diameter of wire 34 and coil 26 (e.g., about 0.001 inch greater than the diameter of the wire and coil). Dimensions "z" and "y" thus may be essentially the same and may be in the range of about 0.005-0.020 inch. This configuration and groove orientation has been found to enhance the grabber member's ability to grab the fastener having a wire diameter range of about 0.0030" to 0.0050" and pull it out of the tissue or material in which it is placed.

Referring to FIGS. 9A-9D, fastener removal is diagrammatically shown. After the fastener wire is placed in the slot 207 of the hook, it is pulled inside the tubular sleeve 212. As the fastener enters the sleeve, it is bent in half and the windings of coil 26 (not shown) surrounding the wire 34 are compressed down towards the ends of the clip. This bending of the clip wire, combined with the compression of the coil on opposite sides of the hook causes the clip to open up enough to be pulled out of the tissue, while minimizing or eliminating the possibility of damaging the tissue. As shown in FIG. 8C, which is a top view of the grabber member, a portion of the grabber member adjacent the hook, has a reduced thickness to provide sufficient space for the fastener to be drawn within the sleeve, while straightening the wire and coil as it is pulled therein. The space "c" on each side of the member generally corresponds to the diameter of the wire and coil and may range, for example, from about 0.004 to 0.010 inch.

The hooked grabbing member can be retracted into the tube as described above. Alternatively, the sleeve 212 can be slidably mounted in housing 206 and attached to flange 216 of button 208. In this variation, one can slide button 208 along slot 214 to slide sleeve 212 over the grabber member, which may be fixed to housing 206, for example, to open or straighten the fastener.

Although a hooked grabbing mechanism is shown, it should be understood that other grabbing mechanisms can be used. Examples of other mechanisms include, but are not limited to, alligator-type jaws 220 or a lasso-like wire loop or snare 234, which may be made from Nitinol, or other suitable material, as shown in FIGS. 10A and 10B, and 11A and 11B, respectively. In the jaws variation, the jaw portion 220a has a reduced width, similar to reduced width portion of the hooked grabber member described above, to allow entry of the fastener as in the hooked grabber as shown in FIG. 8C. In the loop embodiment, the sleeve lumen 212a is sufficiently small to generally straighten the fastener. These grabbing mechanisms will be described in further detail in conjunction with other activators.

Figure 10A:
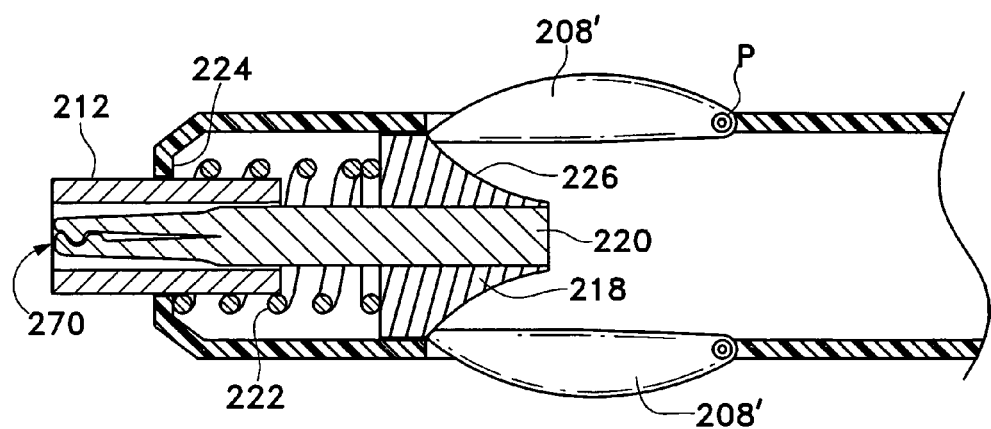
FIGS. 10A and 10B are sectional views of another embodiment of the fastener removal apparatus of the present invention.
Figure 10B:
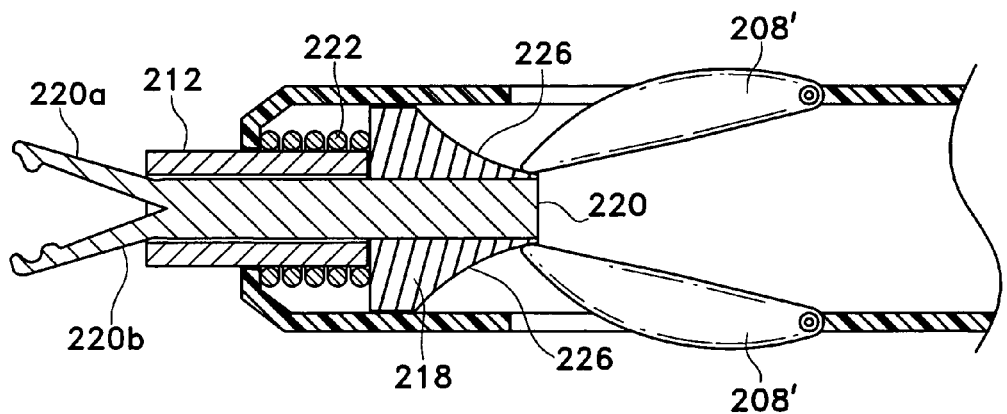

Another grabber displacement mechanism also is shown in FIGS. 10A and 10B in accordance with the present invention. According to this embodiment of the invention, a cam system is used to actuate movement of the grabber member. One or more cams or buttons 208' are pivotally mounted to housing 206 at "P" to engage cam follower member 218, which may be in the form of a frustoconical member surrounding a portion of the grabber member, such as jaws type grabber member 220, as shown, or the hooked type grabber member 204, for example. Grabber member 220 includes jaws 220a and 220b, which, in their relaxed state, are biased toward the configuration shown in FIG. 10B. The biasing, for example, may be accomplished by heat treating the jaws so as to have a memory position in the open configuration. A restraint such as coil spring 222 is placed between the cam follower member 218 and housing annular flange 224 to bias the grabber into the sleeve as shown in FIG. 10A. As the cams or buttons 208' are squeezed or moved toward one another, the buttons engage camming surfaces or interfaces 226 and impart translational motion to the cam follower, which, in turn, forces the grabber member out from sleeve 212 as shown in FIG. 10B.

Figure 10C:
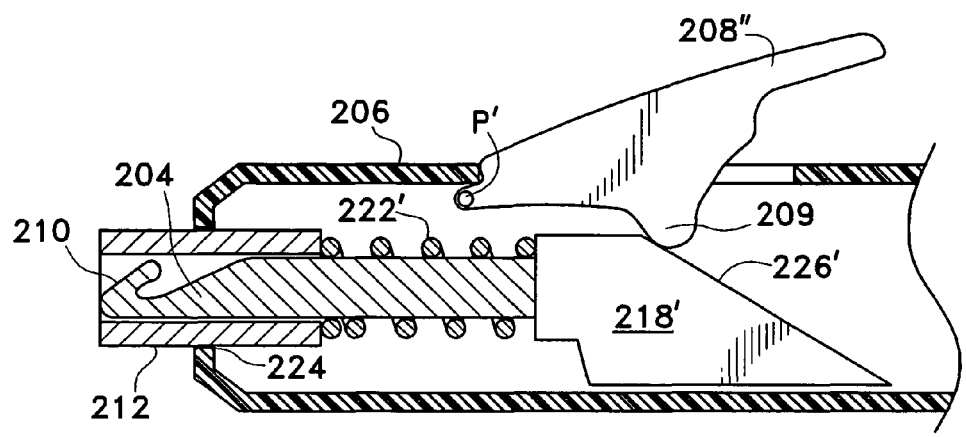
FIGS. 10C and 10D are sectional views of variations of the cam mechanism of FIGS. 10A and 10B in combination with the hooked fastener grabber of FIGS. 8A-C.
Figure 10D:
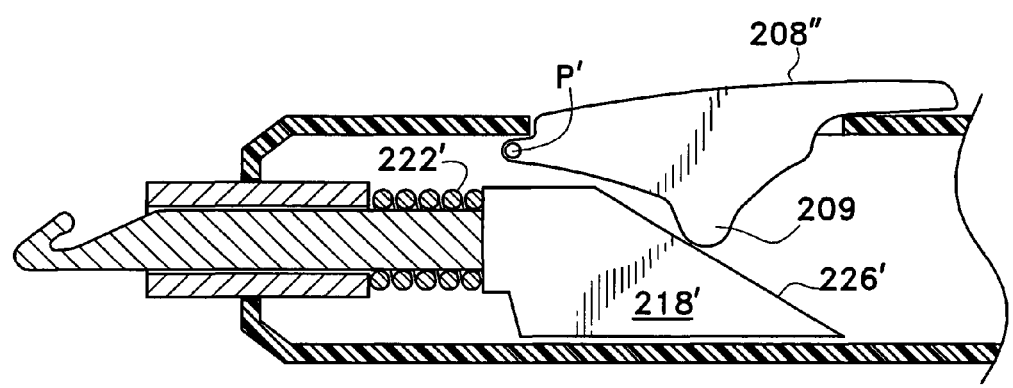

Referring to FIGS. 10C and 10D, a further example of a cam actuated grabber displacement mechanism is shown. In this embodiment, actuator or cam member 208" has a different configuration and is pivotally mounted to housing 206 at pin "p". The actuator or cam member comprises a lever arm and camming projection or interface or roller, or the like, 209, which extends from the lever arm to engage camming surface 226' of cam follower member 218'. Cam follower 218' preferably is secured to one end of the grabber member, which may be hook-type grabber member 204 as shown in the drawings. A restraint, such as coil spring 222', is placed between the cam follower and sleeve 212 to bias the grabber into the sleeve as shown in FIG. 10C. As the actuator 208" is depressed, cam projection 209 moves along camming surface 226' and imparts translational motion to the cam follower member 218', which in turn, forces the grabber member 204 out from sleeve 212 as shown in FIG. 10D.

Although not shown, it should be understood that any of the cam systems shown in FIGS. 10A-D can be arranged or modified to reciprocate the sleeve instead of the grabber member, in which case the grabber member would then be secured to housing 206.

Figure 11A:
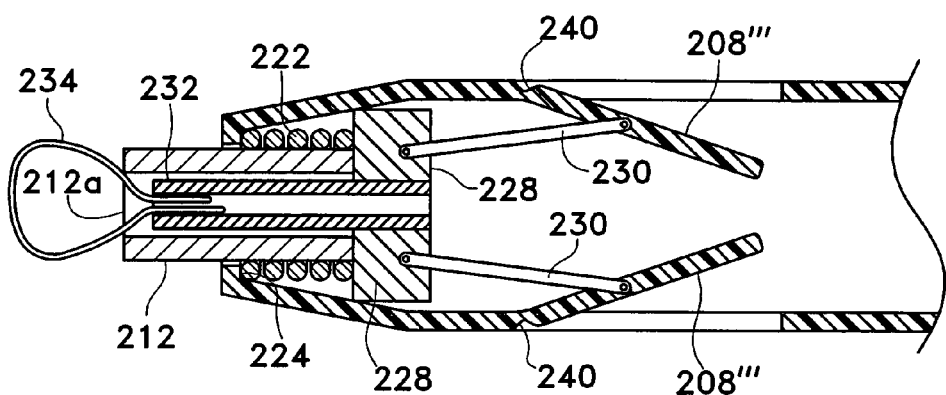
FIGS. 11A and 11B are sectional views of another embodiment of the fastener removal apparatus of the present invention.
Figure 11B:
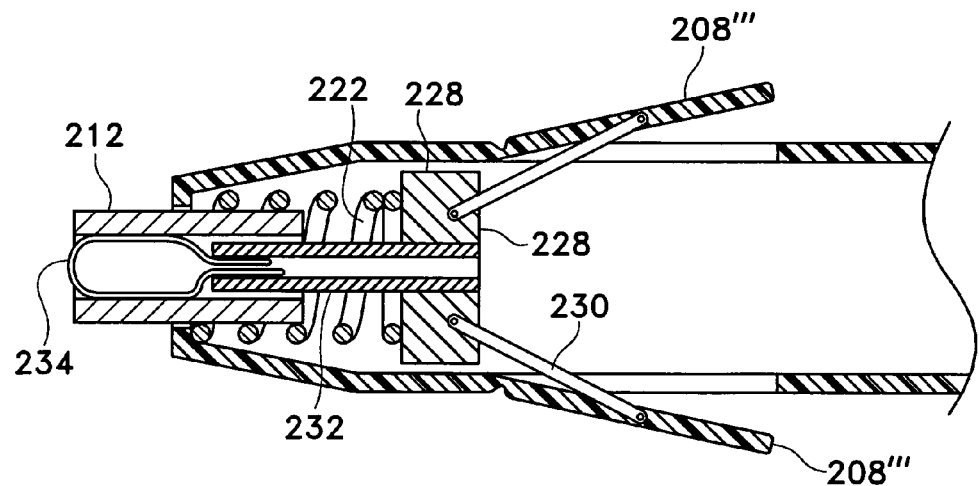

Referring to FIGS. 11A and 11B, another actuating mechanism is shown in combination with a loop grabber. Instead of a camming system, a simple linkage mechanism can impart translational motion to the grabber member 232 when the buttons or actuating levers 208''' are squeezed. These opposing buttons 208''' may be hinged to the handle, 180° apart. The buttons may comprise flaps 208''' extending from the housing and pivotally movable relative thereto at recesses or weakened portions. As in the illustrated embodiment, a circumferential groove 240 can be formed in the housing at the juncture where the flaps extend therefrom to enhance the pivoting capability of the flaps. As the flaps are depressed with the thumb and forefinger, they axially drive or impart translational motion to piston 228 through arms or connecting rods 230. Each arm 230 is pivotally coupled to a flap 208''' and the piston 228 as shown in the drawings. The piston is biased against such axial movement by coil spring 222, which is mounted between the piston and annular flange 224 of the housing. The piston is secured to the elongated grabber member 232 (from which loop 234 extends) so that the grabber member travels or reciprocates with the piston. The number of actuators or buttons may vary. For example, a single button actuator design can be used. It also should be understood that the linkage mechanism can be connected to a movable sleeve, so as to impart translational motion to the sleeve 212 when the buttons are squeezed, in which case the grabber member would be fixed relative to the body. Also, any of the actuating mechanisms and grabber mechanisms described above may be combined and interchanged.

According to further embodiments of the invention, a pair of fastener grabbing heads are provided. The heads are grooved to receive the fastener and at least one of the heads may be beveled to facilitate a wedging action between coil turns of the fastener described above.

Figure 12C:
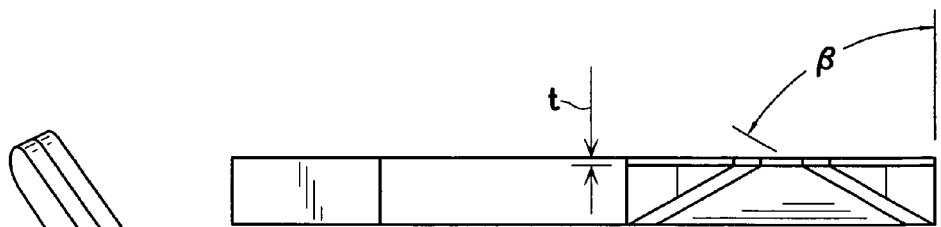
FIGS. 12A, 12B and 12C show another embodiment of fastener removal apparatus of the present invention.
Figure 12A:
Figure 12B:
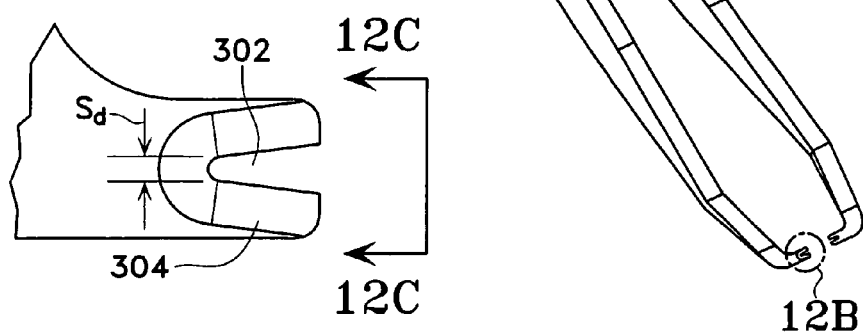

Referring to FIGS. 12A-12B, one embodiment is shown generally comprising a two-part design that when assembled, resembles a pair of surgical tweezers or forceps. This embodiment is generally designated with reference numeral 300. There are two legs to the tweezers 300. The distal tip of each leg tapers down to less than about 0.010 inch thickness ("t", see FIG. 12C) at which point there is approximately a 90° bend inward, toward, the other leg of the tweezers. This bent-in portion 306 extends inward some distance (which may be about 0.1 inch in length) and may be about 0.035" in width. There is a slot cut through this bent-in portion 306 that is the shape of a "V" or a "tapered U" and generally designated with reference numeral 302. The deepest part of the slot $S_d$ is equal to or slightly larger than the diameter of the fastener wire 34. The other end of the slot is greater than the combined diameter of the wire 34 and coil 26 of the fastener. As the fastener moves in toward the closed end of the slot, the beveled portions wedge between coil turns and compresses the coil. The chamber extends all around slot 302. This forms something resembling a two-tined fork. One side of this thin profile member is completely flat, while the other side is chamfered around the "V" profile (See FIG. 12C where β is about 55-65° and may vary depending on the amount of taper to reach dimension "t"). The beveled portion in FIG. 12B is generally designated with numeral 304. The flat sides of the member on each leg face each other, while the chamfered surfaces face outward away from each other. When the tweezers legs are squeezed together, the two flat, profiled, protruding members cross each other, with little or no space between their respective flat surfaces, somewhat resembling the sheering action of two scissors blades.

Figure 13A:
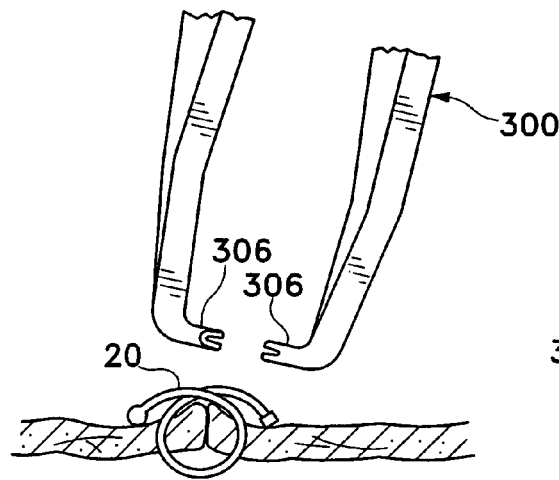
FIGS. 13A, 13B, 13C and 13D diagrammatically illustrate removal of a fastener using the apparatus of FIGS. 12A-C.
Figure 13B:
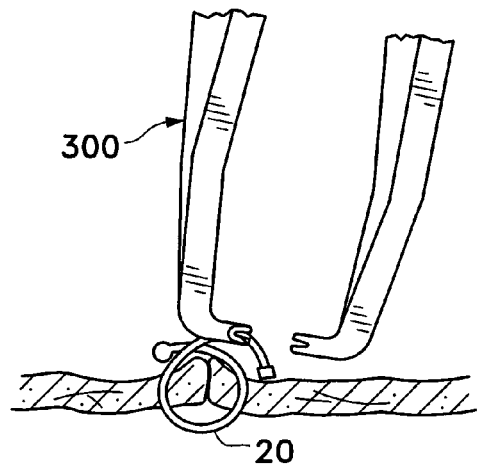
Figure 13C:
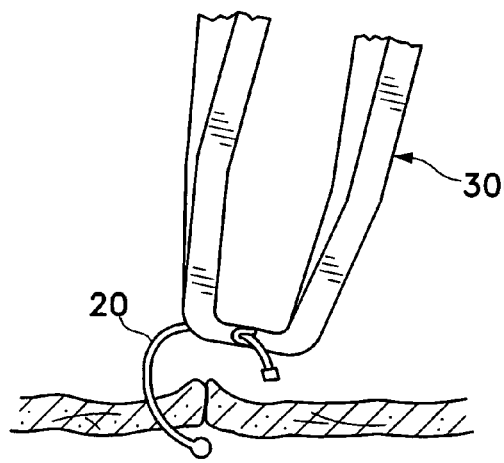
Figure 13D:
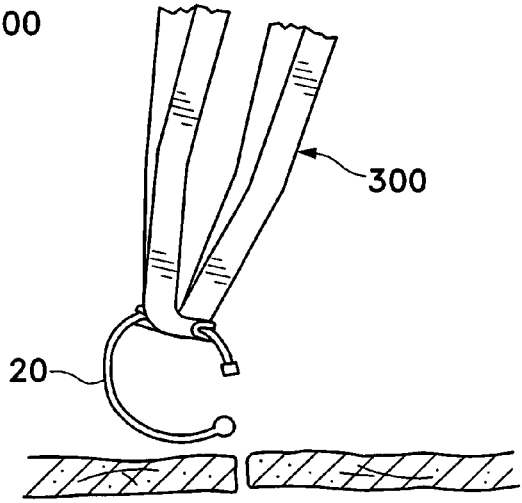

Referring to FIGS. 13A-13C, an example of fastener removal is shown. The surgeon simply brings one of the protruding members (forked parts) of bent-in members 306 in at right angle to the clip, and catches a portion of the clip in the "V" profile (between the tines of the fork, see FIG. 13B). Once an arm of the clip is secured in the bottom of the "V", the tweezers legs are squeezed together. As the two protruding members are brought into proximity (one with the clip in it), the clip becomes engaged in the "V" groove of the second member. At this point the clip is resisting (trapped) between the bottoms of the two "V" grooves. As the tweezers are squeezed further, the edges of the two "V" grooves are forced between the coils of the clip and, thus, come into contact with the clip wire itself. As the tweezers are squeezed further, two things occur: (1) the coils surrounding the clip wire are pushed to the ends (compressed), which is facilitated by the outwardly facing chamfered or beveled surfaces, and this inherently causes the clip to begin to straighten, and (2) the wire begins to bend. The combination of these two things (as in each grabber member apparatus described above) causes the clip to open slightly and loosen its grip on the tissue. This allows the clip to be extracted from the tissue.

Figure 14:
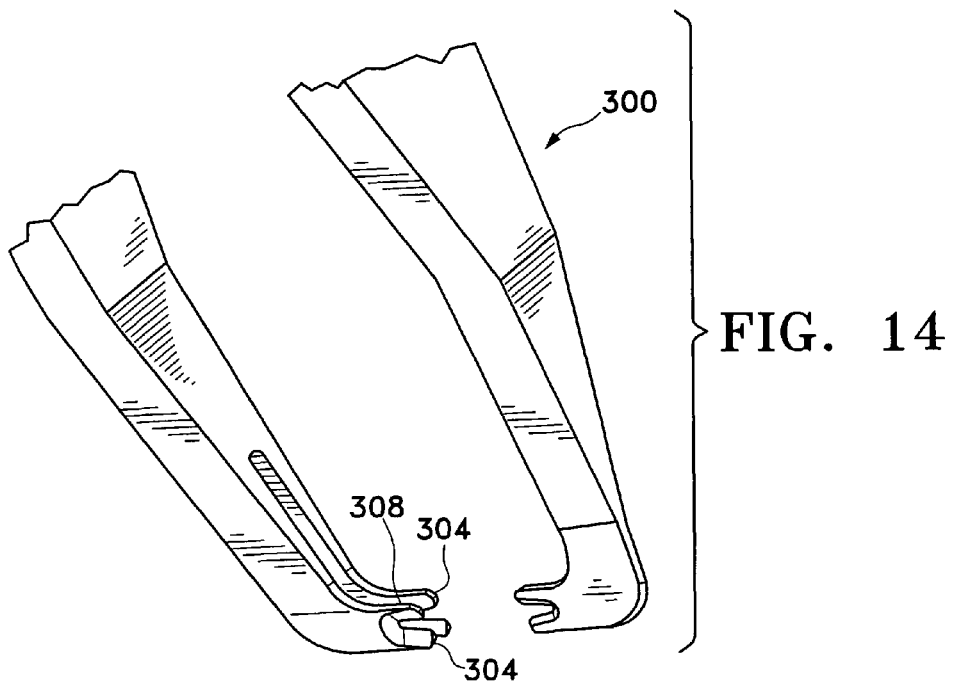
FIG. 14 shows a variation on the apparatus of FIGS. 12A-C.
Figure 15:
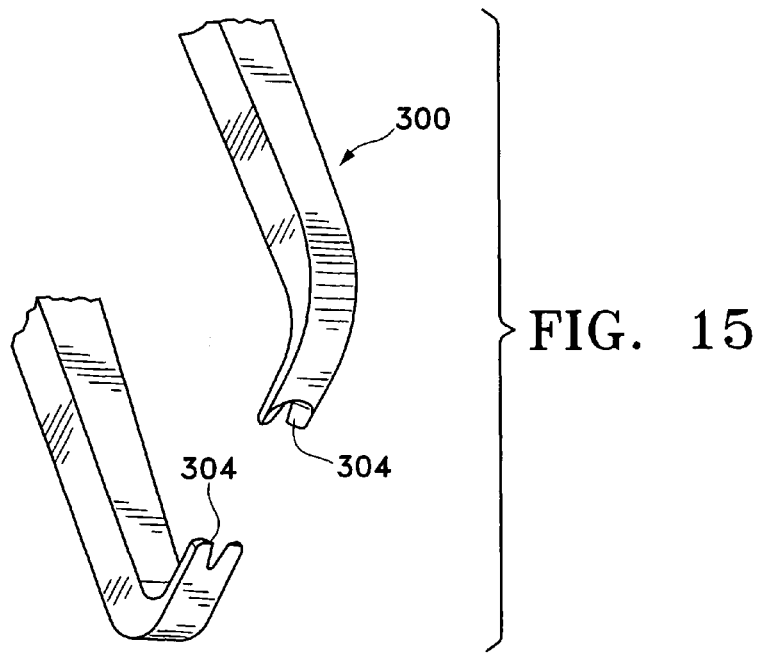
FIG. 15 shows another variation on the apparatus of FIGS. 12A-C.

Other tip configurations also can be used with this tweezers-style removal tool such as the variations shown in FIGS. 14 and 15. Most notably, one leg of the tweezers can have a double edge head at the end of it (FIG. 14). In other words, there are two protruding members, side-by-side at the tip, with a groove 308 existing between them. The groove or gap 308 provides enough space between the two side by side protruding members to allow the opposing protruding member on the other leg to slide between them. This configuration provides a more desirable bend in the clip, thus allowing easier removal. Each of the side by side protruding members has an outwardly facing chamfered or beveled surface 304 and an inwardly facing surface which is generally coplanar with the protruding member, similar to the "flat surfaces described above with regard to FIGS. 13A-D. Both sides of the opposing protruding member are substantially "flat" and coplanar with one another as well as with the "flat" surfaces of the side by side protruding members. Upon actuation, the surfaces of the opposing protruding member pass the inner surfaces of the pair of protruding members at relatively close tolerances to effect bending of the wire without allowing it to slide between the interacting surfaces.

In FIG. 15, the beveled surfaces 304 are rotated about 90° as compared to those in FIG. 12A. In operation, the protruding surfaces operated to grasp and open an clip in essentially the same manner as described with regard to the embodiment of FIG. 12A.

With regard to manufacturing considerations, the apparatus 200 with the "Hook and Slide" design, the design lends itself to standard conventional manufacturing techniques. The hook itself can be made from drawn wire (stainless steel or Nitinol) which has been machined at the tip to form the hook. Wire EDM or laser cutting could also be used to form this hook at the end of the wire. The handle and finger slider (or squeeze buttons) are best injection molded from any number of plastic resins, most likely ABS. The handle halves could then be easily sonic welded together, or bonded, glued, mechanically fixed, or the like. It is conceivable that these parts could be machined from metal or some other material, although this would be a much costlier option. The outer tube which slides over the hook can be extruded or drawn metal or plastic.

The "Sheering Tweezers" design has only two parts, both of which are machined form stainless steel or titanium blanks. The two machined pieces are welded together up near the top of the handle area.

In use, the instrument apparatus 200 is held by the surgeon in similar fashion to a pencil or surgical instrument, such as forceps or a probe. The hook is guided down to the clip and hooked around any part of the clip, preferably at a right angle to the clip. Once the hook is secured on the clip, the hook (with clip) is retracted into the outer tube of the device using the finger slider or squeeze buttons. If it is the wire loop or lasso, the loop must go over one of the free ends of the clip. The loop is then slid up onto the main part of the clip and then retracted (with the clip) into the outer tube using the finger slider or squeeze buttons. At this point the clip is out of the tissue and completely contained within the outer tube. It can be retrieved by reversing the action of the finger slider or squeeze buttons to push it out of the tube.

The "Sheering Tweezers" also is simple to operate. It is held just as any other apical tweezers or forceps would be held. The surgeon guides the distal tip with the protruding member down to the clip and again, preferably at a right angle, slides the protruding member onto the clip. This is done so that the clip is resting in the bottom of the "V" groove, with one tine of the fork under the clip (between clip and tissue) and the other tine over the clip. Once in this position, the legs of the tweezers are squeezed closed. It sometimes requires multiple squeezes to be able to fully extract the clip. The tweezers design is well suited for reuse and sterilization, as it is made of only two parts, which are welded together to form one.

It is further rioted that any of the fasteners, release mechanisms or tissue connector assembly components described in U.S. patent application Ser. Nos. 09/089,884 and 09/090,305, both entitled Tissue Connector Apparatus and Methods and having a filing date of Jun. 3, 1998 and 09/260,623 filed Mar. 1, 1999 and entitled Tissue Connector Apparatus and Methods, may be used. Further, all references cited herein are incorporated by reference in their entirety.

While the above is a complete description of the preferred embodiments of the present invention, various alternatives, modifications and equivalents may be used.

Therefore, the above description should not be taken as limiting the scope of the invention, which is defined by the following claims.

The invention claimed is:

1. A surgical fastener removal apparatus for removing a fastener from a surgical site, the fastener of the type having a loop shaped clip, the apparatus comprising:
    a first member including a surface for engaging a first portion of the clip; and
    a second member comprising a sleeve that defines a lumen that surrounds at least a portion of the first member and terminates at a distal end surface forming a continuous outer diameter such that said lumen is radially closed at said distal end surface, the second member including the distal end surface for engaging a second portion of the clip adjacent to the first portion;
    at least one of the first and second members being movable relative to the other of the first and second members and configured to deform the clip during such movement wherein engagement by distal end surface of the sleeve exerts an opposing force on the clip relative to the force exerted by retraction of the first member relative to the second member;
    and wherein said first member is sized so as to provide a gap surrounding the first member to the sleeve to allow sufficient space for at least a portion of the fastener to be drawn in the sleeve so that a portion of the fastener can be disposed in said second member as the clip is retracted by the first member, the spacing of said second member to said first member causing the clip to deform and substantially release from the surgical site.

2. The apparatus of claim 1, wherein the first member comprises a hook.

3. The apparatus of claim 1, further comprising a body member, the sleeve being immovably mounted to the body member, the first member being movably mounted in the sleeve.

4. The apparatus of claim 1, further comprising a body member, the first member being immovably mounted to the body member, the sleeve being movably mounted to the body member so as to alternately expose and cover the first member.

5. The apparatus of claim 1, wherein:
    said second member is a tubular member and said tubular member forms said sleeve, said tubular member adapted to engage the second portion of the clip adjacent to the first portion upon relative movement between the first member and the tubular member;

the first member has a proximal end and a distal end and includes a groove that forms a hook at the distal end, the hook having a free end and a surface terminating at the free end;

the first member has a longitudinal axis; and the surface extends toward the free end in a direction away from the first member distal end forming an angle of about 50-70 degrees with the longitudinal axis.

6. The apparatus of claim 5 wherein the groove is configured for receiving a portion of the clip.

7. The apparatus of claim 6 wherein the first member is sized so as to provide sufficient space for the fastener to be drawn in the sleeve when disposed in the groove.

8. The apparatus of claim 5 wherein the groove has a width of about 0.005 to 0.020 inch.

9. The apparatus of claim 8 wherein the groove has a depth of about 0.0005 to about 0.020 inch.

10. The apparatus of claim 5 wherein the groove is configured for receiving a portion of the clip.

11. The apparatus of claim 5 wherein the groove has a width of about 0.005 to 0.020 inch.

12. The apparatus of claim 11 wherein the groove has a depth of about 0.005 to 0.020 inch.

13. The apparatus of claim 1 further comprising means for drawing the first member into the sleeve.

14. A surgical fastener removal apparatus for removing a fastener from a surgical site, the fastener of the type having a wire constructed of a shape memory material and a coil wrapped around at least a portion of the wire, the removal apparatus comprising:

a grabber member including a surface for engaging a first portion of the fastener;

a sleeve surrounding at least a portion of the grabber member, the sleeve terminating at a distal end surface for engaging a second portion of the fastener adjacent to the first portion;

the grabber member being movable with respect to the sleeve between a first position in which a distal portion of the grabber member extends outside of the sleeve and a second position in which the distal portion of the grabber member is substantially inside of the sleeve;

the grabber member being able to engage the fastener during retraction from the first position to the second position and exert an opposing force on the fastener relative to a force on the fastener caused by engagement of the fastener to the distal end surface of the sleeve in order to compress the coil and cause the shape memory material of the wire to change from a closed state to an open state in which the fastener substantially releases from the surgical site;

a housing, the sleeve being immovably mounted to the housing, the grabber member being movably mounted in the sleeve;

an actuator slidably connected to the housing and affixed to the grabber member such that user-caused movement of the actuator relative to the housing causes the grabber member to move relative to the sleeve;

wherein said sleeve is sized so as to provide a gap surrounding the grabber member to the sleeve to provide sufficient space so that at least a portion of the fastener can be disposed in said sleeve as the fastener is retracted by the grabber member, the spacing of the sleeve to the grabber member causing the fastener to deform and substantially release from the surgical site.

15. The removal apparatus of claim 14, wherein the grabber member comprises a hook.

16. The removal apparatus of claim 14, wherein:

the grabber member includes a groove that forms a hook at a distal end; and the grabber member has a longitudinal axis; and the groove has a distal surface that is adjacent to the distal end and forms an angle of about 50-70 degrees with the longitudinal axis.

17. The removal apparatus of claim 16 wherein the groove is configured for receiving a portion of fastener.

18. The removal apparatus of claim 16 wherein the groove has a width of about 0.005 to 0.020 inch.

19. The removal apparatus of claim 16 wherein the groove has a width of about 0.005 to 0.020 inch.

20. The removal apparatus of claim 16 wherein the groove has a depth of about 0.005 to 0.020 inch.

21. A surgical system comprising a surgical fastener removal apparatus for removing a fastener from a surgical site, the fastener of the type having a member having a memory set loop configuration and an open configuration and a coil wrapped around at least a portion of said member, said surgical fastener removal apparatus comprising:

a grabber member having a distal portion terminating at a distal end and forming a longitudinal groove extending between, and open relative to, opposing longitudinal sides of said distal portion and adapted to engage a first portion of said fastener, wherein each of said opposing longitudinal sides is flat;

a sleeve surrounding at least a portion of said grabber member and terminating at a distal end surface for engaging a second portion of said fastener adjacent to said first portion;

one of said sleeve and said grabber member being retractable relative to the other between a first position wherein said distal end of the grabber member extends outside of said sleeve and a second position wherein said distal end of the grabber member is closer to said sleeve as compared to when it is in said first position, whereby said grabber member can grab and draw a portion of said fastener into said sleeve in a gap between at least one of said longitudinal sides and an inner surface of said sleeve, with the distal end surface of the sleeve exerting an opposing force on the fastener relative to the force exerted by retraction of the grabber member, said gap being sized such that at least a portion of the fastener to be drawn in the sleeve so that a portion of the fastener can be disposed in said sleeve as the fastener is retracted by the grabber member, the gap causing the fastener to move toward said open configuration.

22. The system 21, wherein said grabber member comprises a hook.

23. The system of claim 21, further comprising a body member, said sleeve being immovably mounted to said sleeve, and said grabber member being movably mounted in said sleeve.

24. The system of claim 21, further comprising a body member, said grabber member being immovably mounted to said body member, and said sleeve being movably mounted to said body member.

25. The system of claim 21 wherein said grabber member is sized so as to provide sufficient space for at least a portion of said fastener to be drawn in said sleeve when said grabber member is in engagement with a portion of said fastener.

26. The system of claim 21 further comprising means for drawing said grabber member into said sleeve.

27. The system of claim 21 wherein said fastener member has enlarged end portions and said coil is disposed therebetween.

* * * * *